(12) United States Patent
Burger et al.

(10) Patent No.: US 9,254,162 B2
(45) Date of Patent: Feb. 9, 2016

(54) DERMAL AND TRANSDERMAL CRYOGENIC MICROPROBE SYSTEMS

(75) Inventors: Keith Burger, San Francisco, CA (US); Ronald Williams, Menlo Park, CA (US); Lisa Elkins, Woodside, CA (US)

(73) Assignee: MyoScience, Inc., Fremont, CA (US)

( * ) Notice: Subject to any disclaimer, the term of this patent is extended or adjusted under 35 U.S.C. 154(b) by 2608 days.

(21) Appl. No.: 11/614,887

(22) Filed: Dec. 21, 2006

(65) Prior Publication Data
US 2008/0154254 A1    Jun. 26, 2008

(51) Int. Cl.
*A61B 18/02* (2006.01)
*A61B 17/00* (2006.01)
*A61B 18/00* (2006.01)

(52) U.S. Cl.
CPC ....... *A61B 18/02* (2013.01); *A61B 2017/00747* (2013.01); *A61B 2018/00452* (2013.01); *A61B 2018/0262* (2013.01); *A61B 2018/0293* (2013.01)

(58) Field of Classification Search
CPC ............. A61B 18/02; A61B 2017/00747; A61B 2018/0293; A61B 2018/0262; A61B 2018/00452
USPC .......................................... 606/20–23, 25, 26
See application file for complete search history.

(56) References Cited

U.S. PATENT DOCUMENTS

| 2,319,542 A | 5/1943 | Hall |
| 2,672,032 A | 3/1964 | Towse |
| 3,226,492 A | 12/1965 | Steinberg |
| 3,289,424 A * | 12/1966 | Lee .................................. 606/22 |
| 3,343,544 A | 9/1967 | Dunn et al. |
| 3,351,063 A * | 11/1967 | Malaker et al. .................. 606/24 |
| 3,507,283 A | 4/1970 | Thomas, Jr. |
| 3,532,094 A | 10/1970 | Stahl |
| 3,664,344 A | 5/1972 | Bryne |
| 3,702,114 A * | 11/1972 | Zacarian .................. 128/200.23 |

(Continued)

FOREIGN PATENT DOCUMENTS

| CA | 2 643 474 | 9/2007 |
| EP | 0043447 A2 | 6/1981 |

(Continued)

OTHER PUBLICATIONS

International Search Report and Written Opinion of PCT Application No. PCT/US08/53876, dated Aug. 15, 2008, 16 pages total.

(Continued)

*Primary Examiner* — David Shay
(74) *Attorney, Agent, or Firm* — Kilpatrick Townsend and Stockton LLP

(57) ABSTRACT

Medical devices, systems, and methods optionally treat dermatological and/or cosmetic defects, and/or a wide range of additional target tissues. Embodiments apply cooling with at least one small, tissue-penetrating probe, the probe often comprising a needle having a size suitable for inserting through an exposed surface of the skin of a patient without leaving a visible scar. Treatment may be applied along most or all of the insertable length of an elongate needle, optionally by introducing cryogenic cooling fluid into the needle lumen through a small, tightly-toleranced lumen of a fused silica fluid supply tube, with the supply tube lumen often metering the cooling fluid. Treatment temperature and/or time control may be enhanced using a simple pressure relief valve coupled to the needle lumen via a limited total exhaust volume space.

29 Claims, 15 Drawing Sheets

(56) References Cited

U.S. PATENT DOCUMENTS

| | | | |
|---|---|---|---|
| 3,795,245 A | 3/1974 | Allen, Jr. et al. | |
| 3,814,095 A | 6/1974 | Lubens | |
| 3,830,239 A | 8/1974 | Stumpf et al. | |
| 3,886,945 A | 6/1975 | Stumpf et al. | |
| 3,889,681 A | 6/1975 | Waller et al. | |
| 3,951,152 A * | 4/1976 | Crandell et al. | 606/25 |
| 3,993,075 A | 11/1976 | Lisenbee et al. | |
| 4,140,109 A | 2/1979 | Savic et al. | |
| 4,207,897 A | 6/1980 | Lloyd et al. | |
| 4,236,518 A | 12/1980 | Floyd | |
| 4,306,568 A | 12/1981 | Torre | |
| 4,376,376 A | 3/1983 | Gregory | |
| 4,404,862 A | 9/1983 | Harris, Sr. | |
| 4,524,771 A | 6/1985 | McGregor et al. | |
| 4,758,217 A | 7/1988 | Gueret | |
| 4,802,475 A | 2/1989 | Weshahy | |
| 4,946,460 A | 8/1990 | Merry et al. | |
| 5,059,197 A * | 10/1991 | Urie et al. | 606/116 |
| 5,200,170 A | 4/1993 | McDow | |
| 5,334,181 A | 8/1994 | Rubinsky et al. | |
| 5,520,681 A * | 5/1996 | Fuller et al. | 606/17 |
| 5,571,147 A | 11/1996 | Sluijter et al. | |
| 5,647,868 A | 7/1997 | Chinn | |
| 5,755,753 A | 5/1998 | Knowlton | |
| 5,814,040 A | 9/1998 | Nelson et al. | |
| 5,879,378 A | 3/1999 | Usui | |
| 5,899,897 A | 5/1999 | Rabin et al. | |
| 5,916,212 A | 6/1999 | Baust et al. | |
| 5,976,505 A | 11/1999 | Henderson | |
| 6,003,539 A | 12/1999 | Yoshihara | |
| 6,032,675 A | 3/2000 | Rubinsky | |
| 6,039,730 A | 3/2000 | Rabin et al. | |
| 6,041,787 A | 3/2000 | Rubinsky | |
| 6,139,545 A | 10/2000 | Utley et al. | |
| 6,141,985 A | 11/2000 | Cluzeau et al. | |
| 6,182,666 B1 | 2/2001 | Dobak, III | |
| 6,196,839 B1 | 3/2001 | Ross | |
| 6,277,099 B1 | 8/2001 | Strowe et al. | |
| 6,277,116 B1 | 8/2001 | Utely et al. | |
| 6,371,943 B1 | 4/2002 | Racz et al. | |
| 6,432,102 B2 | 8/2002 | Joye et al. | |
| 6,494,844 B1 | 12/2002 | Van Bladel et al. | |
| 6,503,246 B1 * | 1/2003 | Har-Shai et al. | 606/23 |
| 6,506,796 B1 | 1/2003 | Fesus et al. | |
| 6,546,935 B2 | 4/2003 | Hooven | |
| 6,551,309 B1 | 4/2003 | LePivert | |
| 6,562,030 B1 | 5/2003 | Abboud et al. | |
| 6,629,951 B2 * | 10/2003 | Laufer et al. | 607/96 |
| 6,648,880 B2 | 11/2003 | Chauvet et al. | |
| 6,669,688 B2 | 12/2003 | Svaasand et al. | |
| 6,672,095 B1 | 1/2004 | Luo | |
| 6,682,501 B1 * | 1/2004 | Nelson et al. | 604/22 |
| 6,706,037 B2 | 3/2004 | Zvuloni et al. | |
| 6,723,092 B2 | 4/2004 | Brown et al. | |
| 6,749,624 B2 | 6/2004 | Knowlton | |
| 6,761,715 B2 | 7/2004 | Carroll | |
| 6,764,493 B1 | 7/2004 | Weber et al. | |
| 6,786,902 B1 | 9/2004 | Rabin et al. | |
| 6,789,545 B2 | 9/2004 | Littrup et al. | |
| 6,840,935 B2 | 1/2005 | Lee | |
| 6,858,025 B2 | 2/2005 | Maurice | |
| 6,902,554 B2 | 6/2005 | Huttner | |
| 6,905,492 B2 | 6/2005 | Zvuloni et al. | |
| 6,960,208 B2 | 11/2005 | Bourne et al. | |
| 7,001,400 B1 | 2/2006 | Modesitt et al. | |
| 7,081,111 B2 | 7/2006 | Svaasand et al. | |
| 7,081,112 B2 * | 7/2006 | Joye et al. | 606/21 |
| 7,083,612 B2 | 8/2006 | Littrup et al. | |
| 7,195,616 B2 | 3/2007 | Diller et al. | |
| 7,217,939 B2 | 5/2007 | Johansson et al. | |
| 7,250,046 B1 | 7/2007 | Fallat | |
| 7,311,672 B2 | 12/2007 | Van Bladel et al. | |
| 7,367,341 B2 | 5/2008 | Anderson et al. | |
| 7,402,140 B2 | 7/2008 | Spero et al. | |
| 7,422,586 B2 | 9/2008 | Morris et al. | |
| 7,578,819 B2 | 8/2009 | Bleich et al. | |
| 2002/0010460 A1 | 1/2002 | Joye et al. | |
| 2002/0013602 A1 | 1/2002 | Huttner | |
| 2002/0045434 A1 | 4/2002 | Masoian et al. | |
| 2002/0068929 A1 | 6/2002 | Zvuloni | |
| 2002/0156469 A1 | 10/2002 | Yon et al. | |
| 2002/0183731 A1 | 12/2002 | Holland et al. | |
| 2002/0193778 A1 | 12/2002 | Alchas et al. | |
| 2003/0036752 A1 | 2/2003 | Joye et al. | |
| 2003/0109912 A1 | 6/2003 | Joye et al. | |
| 2003/0181896 A1 | 9/2003 | Zvuloni et al. | |
| 2003/0220635 A1 | 11/2003 | Knowlton | |
| 2004/0122482 A1 | 6/2004 | Tung et al. | |
| 2004/0143252 A1 | 7/2004 | Hurst | |
| 2004/0162551 A1 | 8/2004 | Brown et al. | |
| 2004/0167505 A1 | 8/2004 | Joye et al. | |
| 2004/0191229 A1 | 9/2004 | Link et al. | |
| 2004/0204705 A1 | 10/2004 | Lafontaine | |
| 2004/0210212 A1 | 10/2004 | Maurice | |
| 2004/0215178 A1 | 10/2004 | Maurice | |
| 2004/0215294 A1 | 10/2004 | Littrup et al. | |
| 2004/0220497 A1 | 11/2004 | Findlay et al. | |
| 2004/0220648 A1 | 11/2004 | Carroll | |
| 2004/0225276 A1 | 11/2004 | Burgess | |
| 2004/0243116 A1 | 12/2004 | Joye et al. | |
| 2005/0004563 A1 | 1/2005 | Racz et al. | |
| 2005/0177147 A1 | 8/2005 | Vancelette et al. | |
| 2005/0177148 A1 | 8/2005 | van der Walt et al. | |
| 2005/0182394 A1 | 8/2005 | Spero et al. | |
| 2005/0203505 A1 | 9/2005 | Megerman et al. | |
| 2005/0203593 A1 | 9/2005 | Shanks | |
| 2005/0209565 A1 | 9/2005 | Yuzhakov et al. | |
| 2005/0209587 A1 | 9/2005 | Joye et al. | |
| 2005/0228288 A1 | 10/2005 | Hurst | |
| 2005/0251103 A1 | 11/2005 | Steffen et al. | |
| 2005/0261753 A1 | 11/2005 | Littrup et al. | |
| 2005/0276759 A1 | 12/2005 | Roser et al. | |
| 2005/0283148 A1 | 12/2005 | Janssen et al. | |
| 2006/0009712 A1 | 1/2006 | Van Bladel et al. | |
| 2006/0015092 A1 | 1/2006 | Joye et al. | |
| 2006/0069385 A1 | 3/2006 | Lafontaine et al. | |
| 2006/0079914 A1 | 4/2006 | Modesitt et al. | |
| 2006/0084962 A1 | 4/2006 | Joye et al. | |
| 2006/0111732 A1 | 5/2006 | Gibbens et al. | |
| 2006/0129142 A1 | 6/2006 | Reynolds | |
| 2006/0142785 A1 | 6/2006 | Modesitt et al. | |
| 2006/0173469 A1 | 8/2006 | Klein et al. | |
| 2006/0189968 A1 | 8/2006 | Howlett et al. | |
| 2006/0190035 A1 | 8/2006 | Hushka et al. | |
| 2006/0200117 A1 | 9/2006 | Hermans | |
| 2006/0212028 A1 | 9/2006 | Joye et al. | |
| 2006/0212048 A1 | 9/2006 | Crainich | |
| 2006/0223052 A1 | 10/2006 | MacDonald et al. | |
| 2006/0224149 A1 | 10/2006 | Hillely | |
| 2007/0060921 A1 | 3/2007 | Janssen et al. | |
| 2007/0088217 A1 | 4/2007 | Babaev | |
| 2007/0129714 A1 | 6/2007 | Elkins et al. | |
| 2007/0156125 A1 | 7/2007 | DeLonzor | |
| 2007/0161975 A1 | 7/2007 | Goulko | |
| 2007/0167943 A1 | 7/2007 | Janssen et al. | |
| 2007/0167959 A1 | 7/2007 | Modesitt et al. | |
| 2007/0179509 A1 | 8/2007 | Nagata et al. | |
| 2007/0198071 A1 | 8/2007 | Ting et al. | |
| 2007/0255362 A1 | 11/2007 | Levinson et al. | |
| 2007/0270925 A1 | 11/2007 | Levinson | |
| 2008/0051776 A1 | 2/2008 | Bliweis et al. | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0183164 A1 | 7/2008 | Elkins et al. | |
| 2008/0200910 A1 | 8/2008 | Burger et al. | |
| 2008/0287839 A1 | 11/2008 | Rosen et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0118722 A1 | 5/2009 | Ebbers et al. | |

(56) References Cited

U.S. PATENT DOCUMENTS

| | | |
|---|---|---|
| 2009/0171334 A1 | 7/2009 | Elkins et al. |
| 2009/0248001 A1 | 10/2009 | Burger et al. |
| 2012/0089211 A1 | 4/2012 | Curtis et al. |

FOREIGN PATENT DOCUMENTS

| | | | |
|---|---|---|---|
| EP | 0 777 123 A2 | | 6/1997 |
| EP | 1 074 273 A1 | | 2/2001 |
| EP | 1377327 B1 | | 9/2007 |
| EP | 1 862 125 | | 12/2007 |
| GB | 1 360 353 A | | 7/1974 |
| GB | 1402632 | | 8/1975 |
| JP | 60-013111 | | 1/1985 |
| JP | 05-038347 | | 2/1993 |
| JP | 10-014656 | | 11/2000 |
| JP | 2001-178737 A | | 7/2001 |
| JP | 2004-511274 A | | 4/2004 |
| JP | 2005-080988 A | | 3/2005 |
| JP | 2006-130055 | | 5/2006 |
| JP | 2008-515469 A | | 5/2008 |
| RU | 2254060 | | 6/2005 |
| WO | WO 97/49344 | | 12/1997 |
| WO | WO 01/97702 | | 12/2001 |
| WO | WO 02/092153 | | 11/2002 |
| WO | WO 2004/039440 A1 | | 5/2004 |
| WO | WO 2004/045434 | * | 6/2004 ........................ 606/25 |
| WO | WO 2004/089460 | | 10/2004 |
| WO | WO 2005/000106 | | 1/2005 |
| WO | WO 2005/079321 A2 | | 9/2005 |
| WO | 2005/096979 A1 | | 10/2005 |
| WO | WO 2006/012128 | | 2/2006 |
| WO | WO 2006/023348 | | 3/2006 |
| WO | 2006/062788 A2 | | 6/2006 |
| WO | 2006/127467 A2 | | 11/2006 |
| WO | WO 2006/125835 | | 11/2006 |
| WO | WO 2007/037326 | | 4/2007 |
| WO | WO 2007/089603 | | 8/2007 |
| WO | WO 2007/129121 | | 11/2007 |
| WO | WO 2007/135629 | | 11/2007 |
| WO | WO 2009/026471 | | 2/2009 |

OTHER PUBLICATIONS

International Preliminary Report on Patentability of PCT Application PCT/US2006/019471, issued Nov. 23, 2007, 4 pages total.

Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

One Med Group, LLC., [webpage] "CryoProbe™", retrieved from the Internet: <<http://www.onemedgroup.com/>> on Feb. 8, 2008, 2 pages total.

Cryosurgical Concepts, Inc., [webpage] "CryoProbe™", retrieved from the Internet: << http://www.cryo-surgical.com//>> on Feb. 8, 2008, 2 pages total.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

Advanced Cosmetic Intervention, Inc. [webpage], retrieved from the Internet: <<http://www.acisurgery.com>>, copyright 2007, 1 page.

Utley et al., "Radiofrequency Ablation of the Nerve to the Corrugator Muscle for the Elimination of Glabellar Furrowing," Arch. Facial Plastic Surgery 1: 46-48, 1999.

International Search Report of PCT Application PCT/US07/87893, dated Jun. 18, 2008, 14 pages total.

Yang et al., "Apoptosis induced by cryo-injury in human colorectal cancer cells is associated with mitochondrial dysfunction.," Int J Cancer. Jan. 20, 2003;103(3):360-369.

European Extended Search Report for European Patent Application No. 07865802.8, mailed Jun. 22, 2012, 8 pages.

European Examination Report for European Patent Application No. 08729785.9, mailed Feb. 13, 2012, 5 pages.

European Extended Search Report for European Patent Application No. 09835792.4, mailed May 15, 2012, 10 pages.

European Extended Search Report for European Patent Application No. 09835799.9, mailed May 11, 2012, 7 pages.

Foster et al., "Radiofrequency Ablation of Facial Nerve Branches Controlling Glabellar Frowning", Dermatol Surg. Dec. 2009; 35(12):1908-1917.

International Search Report and Written Opinion of PCT Application PCT/US2011/064740, mailed Apr. 6, 2012, 10 pages.

Japanese Office Action for Japanese Patent Application No. 2009-543133 mailed Aug. 27, 2012, 7 pages.

Dasiou-Plankida, "Fat injections for facial rejuvenation: 17 years experience in 1720 patients," Journal of Cosmetic Dermatology, Oct. 22, 2004; 2(3-4): 119-125.

Har-Shai et al., "Effect of skin surface temperature on skin pigmentation during contact and intralesional cryosurgery of hypertrophic scars and Kleoids," Journal of the European Academy of Dermatology and Venerology 21 (2): 191-198.

Magalov et al., "Isothermal volume contours generated in a freezing gel by embedded cryo-needles with applications to cryo-surgery," Cryobiology, Oct. 2007; 55(2):127-137.

Rewcastle et al., "A model for the time dependent three-dimensional thermal distribution within iceballs surrounding multiple cryoprobes," Med Phys. Jun. 2001;28(6):1125-1137.

\* cited by examiner

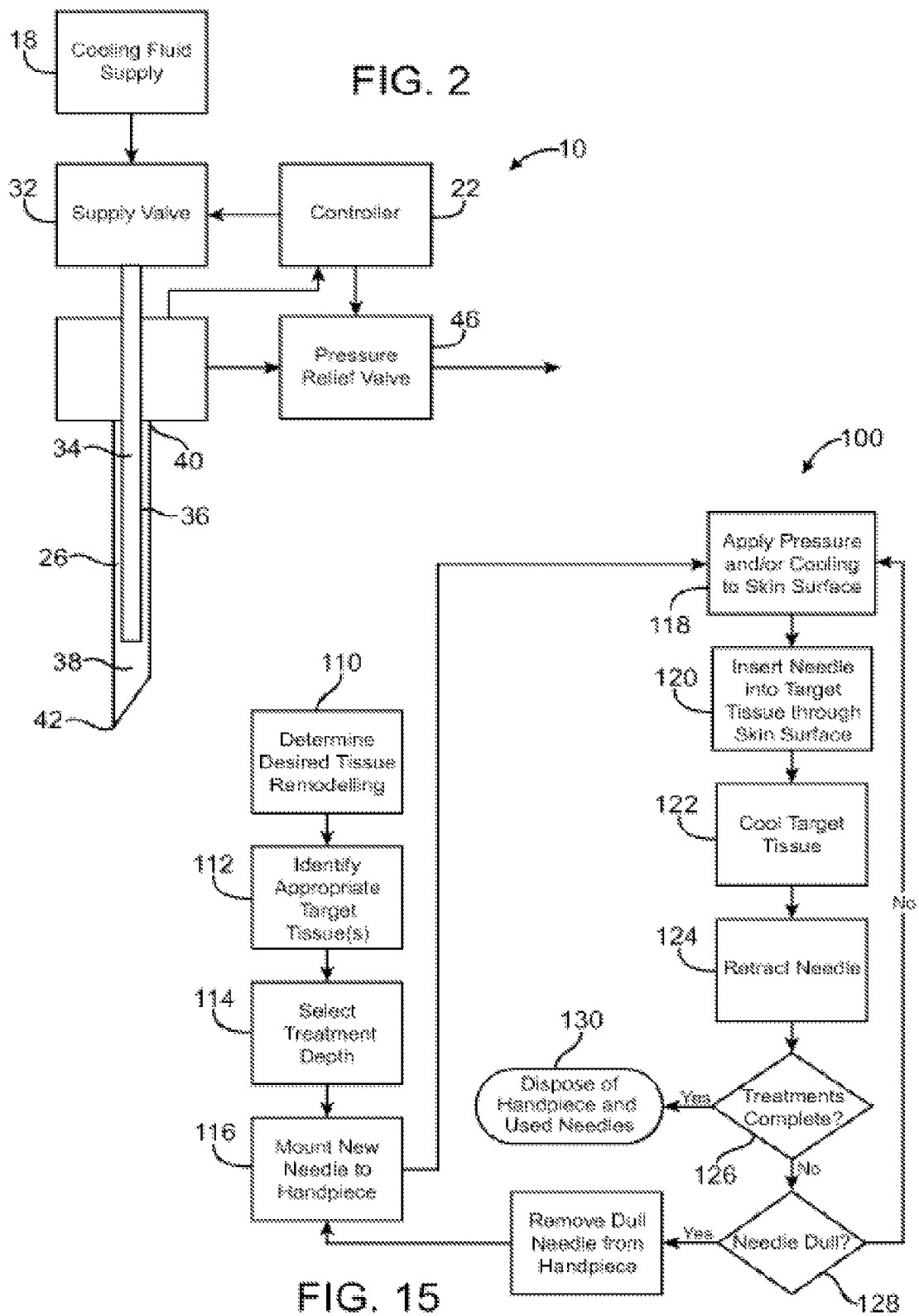

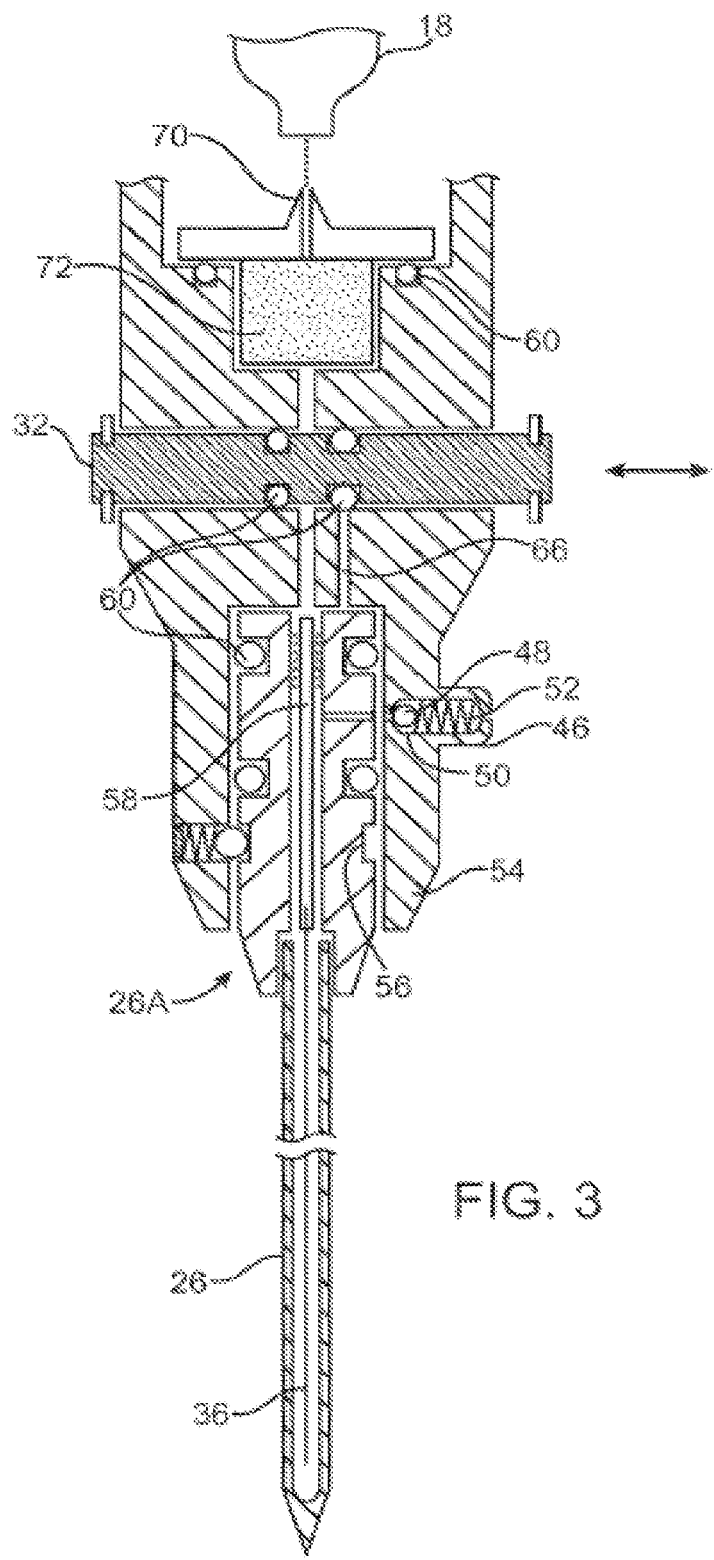

Section AA

Section BB

DERMAL AND TRANSDERMAL CRYOGENIC MICROPROBE SYSTEMS

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention is generally directed to medical devices, systems, and methods, particularly for cooling-induced remodeling of tissues. Embodiments of the invention include devices, systems, and methods for applying cryogenic cooling to dermatological tissues so as to selectively remodel one or more target tissues along and/or below an exposed surface of the skin. Embodiments may be employed for a variety of cosmetic conditions, optionally by inhibiting undesirable and/or unsightly effects on the skin (such as lines, wrinkles, or cellulite dimples) or on other surrounding tissue. The remodeling of the target tissue may achieve a desired change in its behavior or composition.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary innervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, it would be desirable to provide improved medical devices, systems, and methods, particularly for treatment of wrinkles, fat, cellulite, and other cosmetic defects. It would be particularly desirable if these new techniques provided an alternative visual appearance improvement mechanism which could replace and/or compliment known bioactive and other cosmetic therapies, ideally allowing patients to decrease or eliminate the injection of toxins and harmful cocktails while providing similar or improved cosmetic results. It would also be desirable if such techniques were performed percutaneously using only local or no anesthetic with minimal or no cutting of the skin, no need for suturing or other closure methods, no extensive bandaging, and limited or no bruising or other factors contributing to extended recovery or patient "down time". It would further be desirable to provide new devices, systems, and methods for treatment of other cosmetic and/or dermatological conditions (and potentially other target tissues), particularly where the treatments may be provided with greater accuracy and control, less collateral tissue injury and/or pain, and greater ease of use.

BRIEF SUMMARY OF THE INVENTION

The present invention generally provides improved medical devices, systems, and methods. Embodiments may be particularly well suited for the treatment of dermatological and/or cosmetic defects, and alternative embodiments may be configured for treatment of a wide range of target tissues. Some embodiments of the present invention apply cooling with at least one small, tissue-penetrating probe, the probe often comprising a needle having a size suitable for inserting through an exposed surface of the skin of a patient without leaving a visible scar. The cooling may remodel one or more target tissue so as to effect a desired change in a composition of the target tissue and/or a change in its behavior. Treatment may be applied along most or all of the insertable length of an elongate needle, optionally by introducing cryogenic cooling fluid into the needle lumen through a small, tightly-toleranced lumen of a fused silica fluid supply tube, with the supply tube lumen often metering the cooling fluid. Treatment temperature and/or time control may be enhanced using a simple pressure relief valve coupled to the needle lumen with a limited total exhaust volume space.

In a first aspect, the invention provides a system for treating a target tissue of a patient. The system comprises a needle having a proximal end, a distal end, and a lumen therebetween, with the needle having a 16 gauge or smaller needle size. A cooling fluid supply lumen extends distally within the needle, and a cooling fluid source is coupleable to the supply lumen to direct cooling fluid flow into the needle lumen so that liquid from the cooling flow vaporizes within the target tissue when the needle extends into the target tissue.

In many cases, the needle will have a 25 gauge or smaller needle size and a tip for penetrating a skin surface. Exemplary embodiments comprise 30 gauge or smaller needles. The needles will often comprise metallic structures, typically comprising stainless steel hypotube. The supply lumen may reside in a non-metallic supply tube, with the exemplary supply tube comprising fused silica. A polymer may be disposed over the fused silica, with an outer diameter of the polymer preferably being less than 800 µm, and ideally less than 200 µm. The supply tube generally extends in cantilever distally into the needle lumen so that it will be advantageous to employs supply tubes of fused silica or other materials with sufficient stiffness to inhibit flow induced buckling of the supply tube within the needle lumen. The exemplary fused silica supply tubes are particularly well suited for use within high aspect ratio needles, such as those having a ratio between an insertable length of the needle to an outer size of the needle of more than 20, the aspect ratio optionally being at least 100, although shorter needles may also be used. In many embodiments, the supply lumen has an inner diameter of less than 100 µm, often being less than 50 µm, and preferably being less than 35 µm, and the exemplary non-metallic supply tubes provide good system durability in the demanding cryogenic environment within the needle despite their very small size.

A handle may support the needle, the supply lumen, and the fluid source for manual manipulation and positioning of the system during treatment. A pressure relief valve will often be in fluid communication with the needle lumen so as to control a pressure of the vaporizing cooling flow within the needle. This can effectively provide cooling of the target tissue to a treatment temperature within a desired treatment temperature range. In the exemplary embodiment, nitrous oxide cooling liquid is maintained at about room temperature in a sealed canister prior to use, with the canister being pierced to initiate cooling flow into the needle lumen. The vaporizing liquid drives the cooling fluid through the supply tube and into the needle so that the needle lumen includes a mixture of liquid and gas. The flow can be metered primarily by a flow resistance of the supply lumen, the flow optionally being substantially entirely metered by the flow resistance, particularly when using the exemplary small lumen diameter fused silica supply tubes (as they can have quite uniform lumen diameters). In some embodiments, the flow may not be actively modulated between the fluid source and the needle lumen during cooling.

It will often be advantageous to limit a size of the cooling fluid exhaust pathway to improve treatment temperature and time control. In some embodiments, the pressure relief valve comprises a biasing spring mechanically urging a valve member against a valve seat so as to maintain pressure of the needle lumen within a desired pressure range. An exhaust volume may be defined along the cooling fluid path between the supply lumen and the valve seat, with the biasing spring typically being disposed outside the exhaust volume to minimize the size of the exhaust volume and. The exhaust volume is preferably less than about 0.05 in$^3$, typically being less than 0.01 in$^3$, ideally being less than 0.005 in$^3$.

It will also be beneficial to limit the effect of liquid cooling fluid disposed along the intake pathway when the valve is shut off. In general, a supply valve will be disposed between the supply lumen and the fluid source. The cooling fluid supply volume along the cooling fluid path between the needle lumen and the supply valve may be vented by the supply valve. More specifically, the valve may have a first configuration and a second configuration, the valve in the first configuration providing fluid communication between the fluid source and the supply volume, the valve in the second configuration inhibiting the cooling flow and venting the supply volume so as to limit cooling fluid vaporization within the needle lumen after the valve moves from the first configuration to the second configuration.

At least one distally oriented skin engaging surface will often be provided. For example, a handpiece body may support the needle, and the at least one skin engaging surface may be supported by the handpiece body so as to engage the skin surface before and/or during cooling of the target tissue. In some embodiments, an insertable length of the needle between the distal end of the needle and the at least one skin engaging surface may be selectably alterable, for example, by providing a plurality of spacer bodies, the spacer bodies having differing thicknesses. The user can select an effective needle length by mounting an appropriate spacer to the handpiece and/or needle. Optionally, the skin engaging surface may be extendable distally beyond the needle to avoid unintentional needle sticks, apply cooling to the skin adjacent the needle insertion location, or pressure to dull any needle insertion pain, or the like. Hence, an articulatable support may couple the skin engaging surface to the needle so the skin engaging surface applies a pain dulling pressure to the skin before and/or during skin penetration by the needle. To cool the skin engaging surface, it may be thermally coupled to a skin cooling chamber, wherein a skin cooling port directs cooling fluid from the fluid source into the skin cooling chamber. Where the skin surface is cooled to a more moderate temperature than the target tissue engaged by the needle, the skin cooling chamber can have a higher operating pressure than the needle lumen. For example, the skin engaging surface may be configured to cool the skin to a more moderate, safe temperature (often being above $-15°$ C., optionally being above $-10°$ C., in some cases being above $0°$ C.) to inhibit inflammation, while the needle is configured to more significantly cool the target tissue (typically to significantly below $0°$ C., and in many cases being below $-15°$ C.) to induce necrosis.

Cooling rates may be tailored within a wide range to promote desired therapeutic results. For example, when the flow is initiated, an outer surface of the needle engaging the target tissue may cool at a rate of more than about $25°$ C./sec (optionally being more than about $40°$ C./sec) so as to promote intracellular ice formation and necrosis of the target tissue. In such embodiments, an array of needles can be coupled to the fluid source can have similar cooling rates to promote intracellular ice formation and necrosis of the target tissue between the needles. Alternatively, lower engaged tissue cooling rates may be used to help promote osmotic effects that inhibit intracellular ice formation and associated necrosis. A variety of more sophisticated embodiments may make use of multiple cooling states, such as by providing a controller coupled with the needle lumen via a valve. The controller might, for example, have a first configuration for providing an initial cooling state and a second configuration for providing a treatment temperature in a target range. The treatment temperature might be established by generating a target treatment pressure in the lumen, while the initial cooling state could be configured (for example) to induce gradual cooling of the needle using an intermediate treatment pressure in the needle lumen that is higher than the target treatment pressure.

A variety of refinements may be included to increase the efficiency and/or efficacy of the system. For example, while many embodiments may employ needles having circular cross-sections, an outer surface of the needle may optionally have an elongate cross-section to promote cooling of a greater volume of the target tissue. In some embodiments, a proximal cross-section of the needle might be circular to limit cooling adjacent the skin, with the elongate cross-section comprising an elliptical cross-section to enhance cooling along the target tissue. The distal end of such a needle might have a sharpened cutting edge. The cooling fluid may, when vaporizing within the needle lumen, cool an outer surface of the needle to a temperature in a treatment temperature range substantially throughout an entire insertable length of the needle extending from the distal end of the needle to the proximal end of the needle, such that a target tissue extending to the skin surface can be treated.

In another aspect, the invention provides a method for treating a target tissue of a patient. The method comprises advancing a needle distally to penetrate into the target tissue, the needle having a lumen and a less than 16 gauge needle size. A cooling fluid flow is directed distally within the target tissue through a supply lumen within the needle. The target tissue is cooled by vaporizing a liquid from the cooling flow within the needle lumen.

BRIEF DESCRIPTION OF THE DRAWINGS

FIG. 2 schematically illustrates components that may be included in the treatment system.

FIG. 3 is a schematic cross-sectional view of an embodiment of a distal portion of the probe and system of FIG. 1B, showing a replaceable needle and an pressure relief valve with a limited exhaust volume.

FIG. 3A illustrates an exemplary fused silica cooling fluid supply tube for use in the replaceable needle of FIG. 3.

FIG. 15 is a flow chart schematically illustrating a method for treatment using the disposable cryogenic probe and system of FIG. 1B.

DETAILED DESCRIPTION OF THE INVENTION

The present invention provides improved medical devices, system, and methods. Embodiments of the invention will facilitate remodeling of tissues disposed at and below the skin, optionally to treat a cosmetic defect, a lesion, a disease state, and/or so as to alter a shape of the overlying skin surface.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., optionally so as to provide a permanent treatment that limits or avoids inflammation and mobilization of skeletal muscle satellite repair cells. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling for treatment of cosmetic and other defects may be found in co-pending U.S. patent application Ser. No. 11/295,204, filed on Dec. 5, 2005 and entitled "Subdermal Cryogenic Remodeling of Muscle, Nerves, Connective Tissue, and/or Adipose Tissue (Fat)," the full disclosure of which is incorporated herein by reference.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms. Hence, a variety of embodiments may be provided.

Figure 1A:
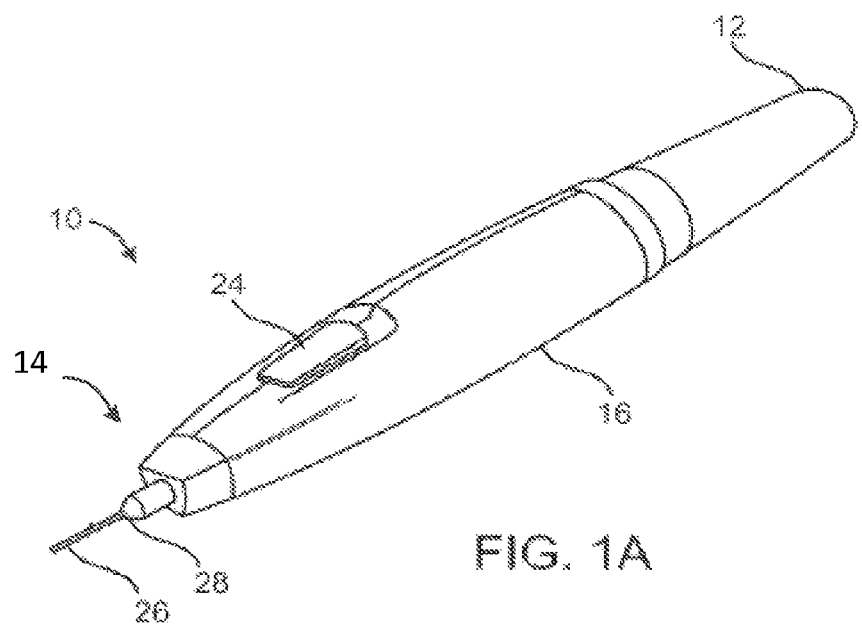
FIG. 1A is a perspective view of a self-contained subdermal cryogenic remodeling probe and system, according to an embodiment of the invention.
Figure 1B:
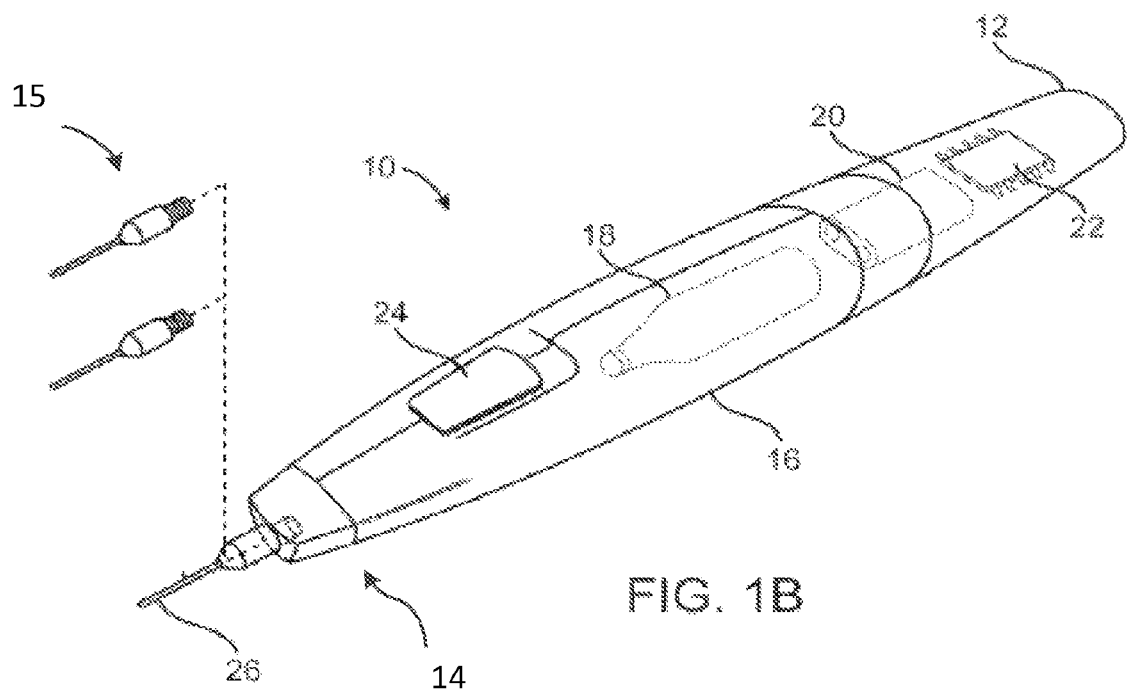
FIG. 1B is a partially transparent perspective view of the self-contained probe of FIG. 1A, showing internal components of the cryogenic remodeling system and schematically illustrating replacement treatment needles 15 for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and shape suitable for supporting in a hand of a surgeon or other system operator. As can be seen most clearly in FIG. 1B, a cryogenic cooling fluid supply 18 and electrical power source 20 are found within housing 16, along with a circuit 22 having a processor for controlling cooling applied by self-contained system 10 in response to actuation of an input 24. Some embodiments may, at least in part, be manually activated, such as through the use of a manual supply valve and/or the like, so that processors, electrical power supplies, and the like may be absent.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 30 g needle having a sharpened distal end that is axially sealed. Probe 26 may have an axial length between distal end 14 of housing 16 and the distal end of the needle of between about ½ mm and 5 cm, preferably having a length from about 1 cm to about 3 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, typically comprising a 25 g or smaller needle.

Addressing some of the components within housing 16, the exemplary cooling fluid supply 18 comprises a cartridge containing a liquid under pressure, with the liquid preferably having a boiling temperature of the less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A valve (not shown) may be disposed along the cooling fluid flow path between cartridge 18 and probe 26, or along the cooling fluid path after the probe so as to limit the temperature, time, rate of temperature change, or other cooling characteristics. The valve will often be powered electrically via power source 20, per the direction of processor 22, but may at least in part be manually powered. The exemplary power source 20 comprises a rechargeable or single-use battery.

The exemplary cooling fluid supply 18 comprises a single-use cartridge. Advantageously, the cartridge and cooling fluid therein may be stored and/or used at (or even above) room temperature. The cartridges may have a frangible seal or may be refillable, with the exemplary cartridge containing liquid $N_2O$. A variety of alternative cooling fluids might also be used, with exemplary cooling fluids including fluorocarbon refrigerants and/or carbon dioxide. The quantity of cooling fluid contained by cartridge 18 will typically be sufficient to treat at least a significant region of a patient, but will often be less than sufficient to treat two or more patients. An exemplary liquid $N_2O$ cartridge might contain, for example, a quantity in a range from about 7 g to about 30 g of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Referring now to FIG. 2, the flow of cryogenic cooling fluid from fluid supply 18 is controlled by a supply valve 32. Supply valve may comprise an electrically actuated solenoid valve or the like operating in response to control signals from controller 22, and/or may comprise a manual valve. Exemplary supply valves may comprise structures suitable for on/off valve operation, and may provide venting of the cooling fluid path downstream of the valve when cooling flow is halted so as to limit residual cryogenic fluid vaporization and cooling. More complex flow modulating valve structures might also be used in other embodiments.

The cooling fluid from valve 32 flows through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure 36a having a polymer coating 36b (see FIG. 3A) and extends in cantilever into the needle lumen 38. Supply tube 36 may have an inner lumen with an effective inner diameter 36c of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size 36 d of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26.

Figure 12:
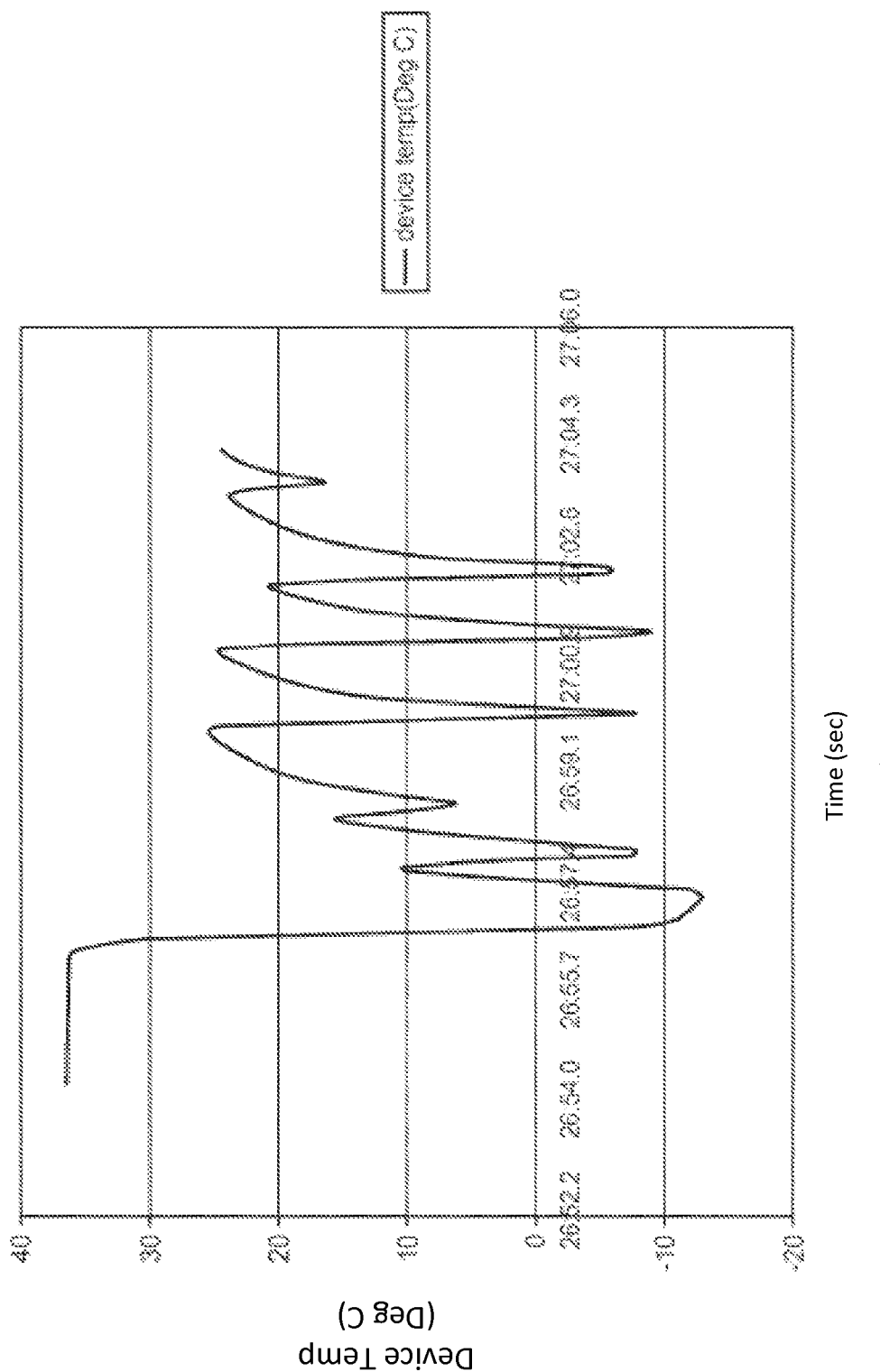
FIG. 12 graphically illustrates non-uniform cooling that can result from inadequate evaporation space within a small cryogenic needle probe.

Though supply tubes 36 having outer jackets of polyimide (or other suitable polymer materials) may bend within the surrounding needle lumen 38, the supply tube should have sufficient strength to avoid collapsing or excessive blow back during injection of cooling fluid into the needle. Polyimide coatings may also provide durability during assembly and use, and the fused silica/polymer structures can handle pressures of up to 100 kpsi. The relatively thin tubing wall and small outer size of the preferred supply tubes allows adequate space for vaporization of the nitrous oxide or other cooling fluid within the annular space between the supply tube 36 and surrounding needle lumen 38. Inadequate space for vaporization might otherwise cause a buildup of liquid in that annular space and inconsistent temperatures, as illustrated in FIG. 12. Exemplary structures for use as supply tube 36 may include the flexible fused silica capillary tubing sold commercially by Polymicro Technologies, LLC of Phoenix, Ariz. under model names TSP, TSG, and TSU, optionally including model numbers TSP 020090, TSP040105, and/or others.

Referring now to FIGS. 2 and 3, the cooling fluid injected into lumen 38 of needle 26 will typically comprises liquid, though some gas may also be injected. At least some of the liquid vaporizes within needle 26, and the enthalpy of vaporization cools the tissue engaged by the needle. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body 48 (here in the form of a ball bearing) urged against a valve seat 50 by a biasing spring 52.

Figure 4:
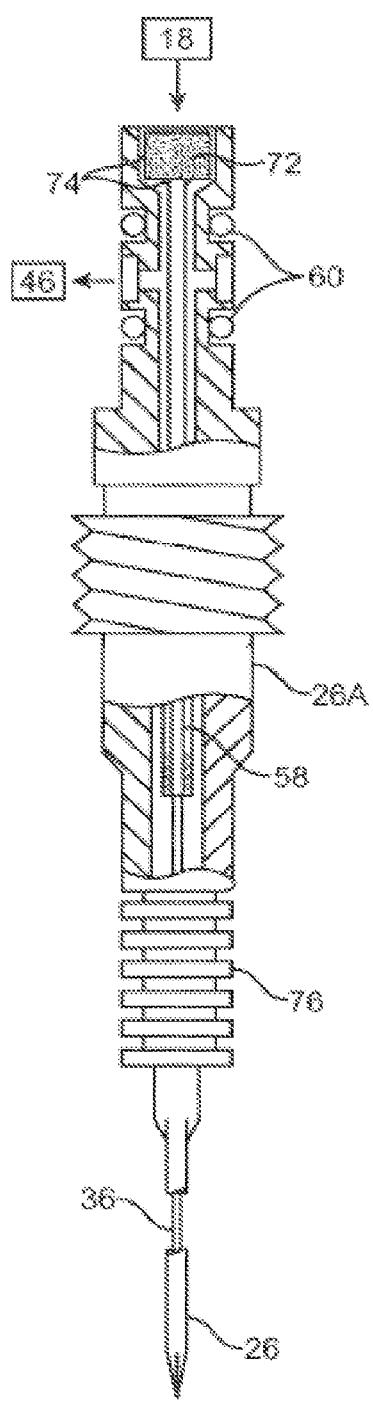
FIG. 4 is a more detailed view of a replaceable needle assembly for use in the system of FIGS. 1A and 1B.

During initiation of a cooling cycle, a large volume along the cooling fluid pathway between the exit from the supply tube and exit from the pressure relief valve 46 may cause excessive transients. In particular, a large volume in this area may result in initial temperatures that are significantly colder than a target and/or steady state temperature, as can be seen in FIG. 13D. This can be problematic, particularly when (for example) the target temperature is only slightly warmer than an undesirable effect inducing temperature, such as when remodeling through apoptosis or the like while seeking to inhibit necrosis. To limit such transients, the pressure relief valve 46 may be integrated into a housing 54 supporting needle 26, with the valve spring 52 being located outside the valve seat (and hence the pressure-control exit from pressure relief valve 46). Additionally, where needle 26 is included in a replaceable needle assembly 26A, pressure relief valve 46 is also located adjacent the interface between the needle assembly and probe handpiece housing 54. A detent 56 may be engaged by a spring supported catch to hold the needle assembly releasably in position, and the components of the needle assembly 26A (such as a brass or other metallic housing, a polyimide tubing 58, needle 26, and the like) may be affixed together using adhesive. Alternatively, as illustrated in FIGS. 1B and 4, the needle assembly and handpiece housing may have corresponding threads for mounting and replacement of the needle assembly. O-rings 60 can seal the cooling fluid pathway.

Figure 13A:
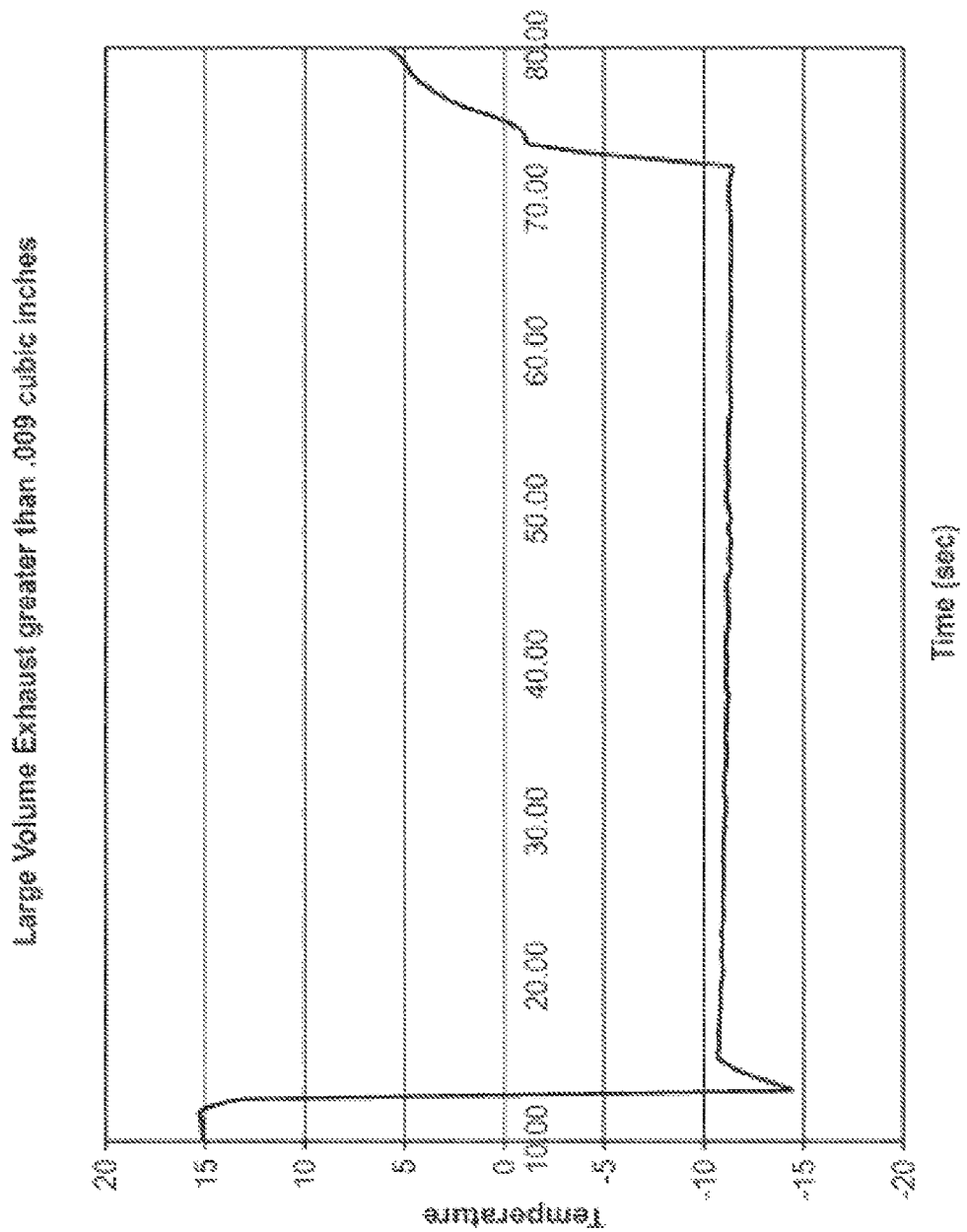
FIGS. 13A-13D graphically illustrate effects of changes in exhaust volume on the cooling response by a small cryogenic needle probe.
Figure 13B:
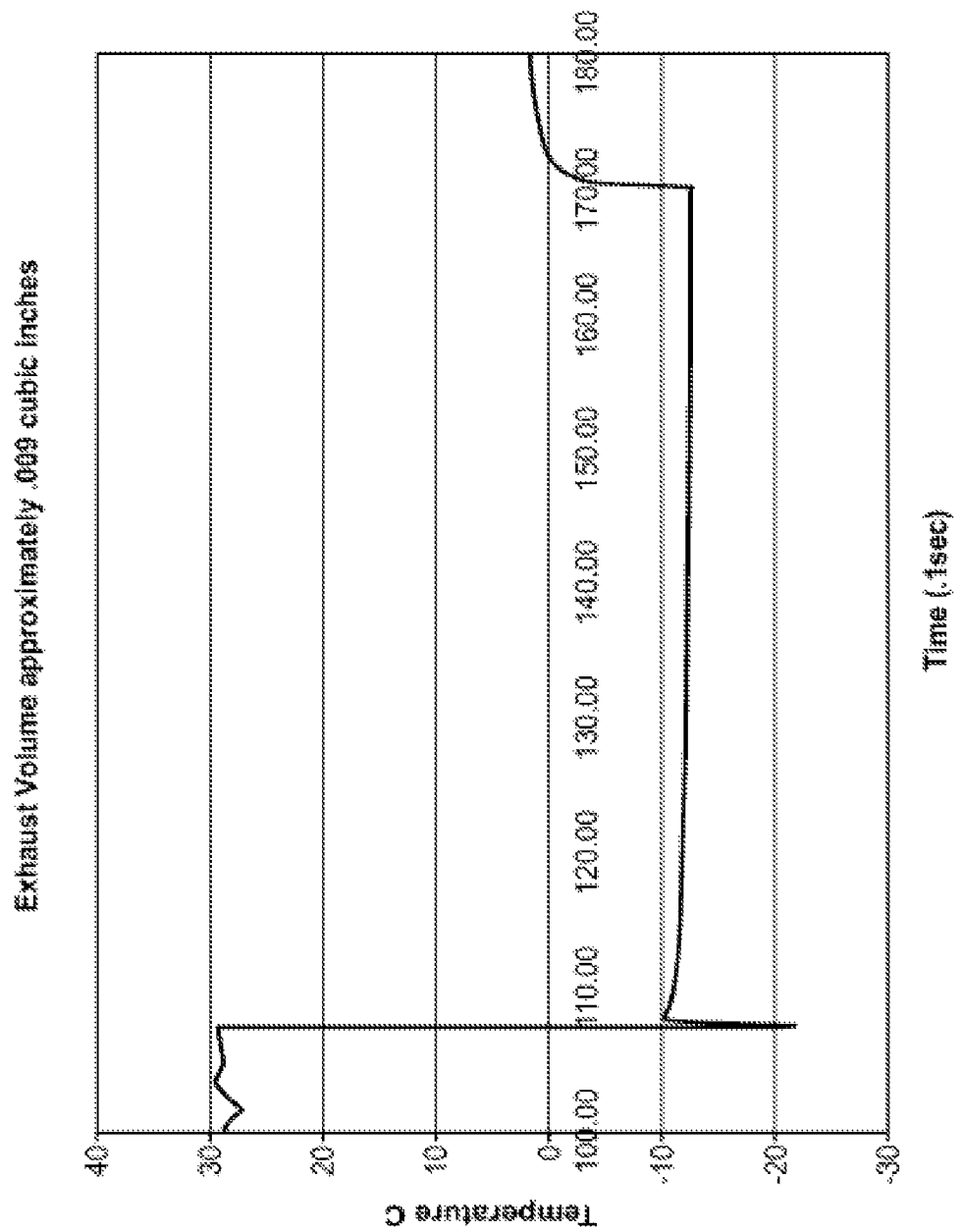
Figure 13C:
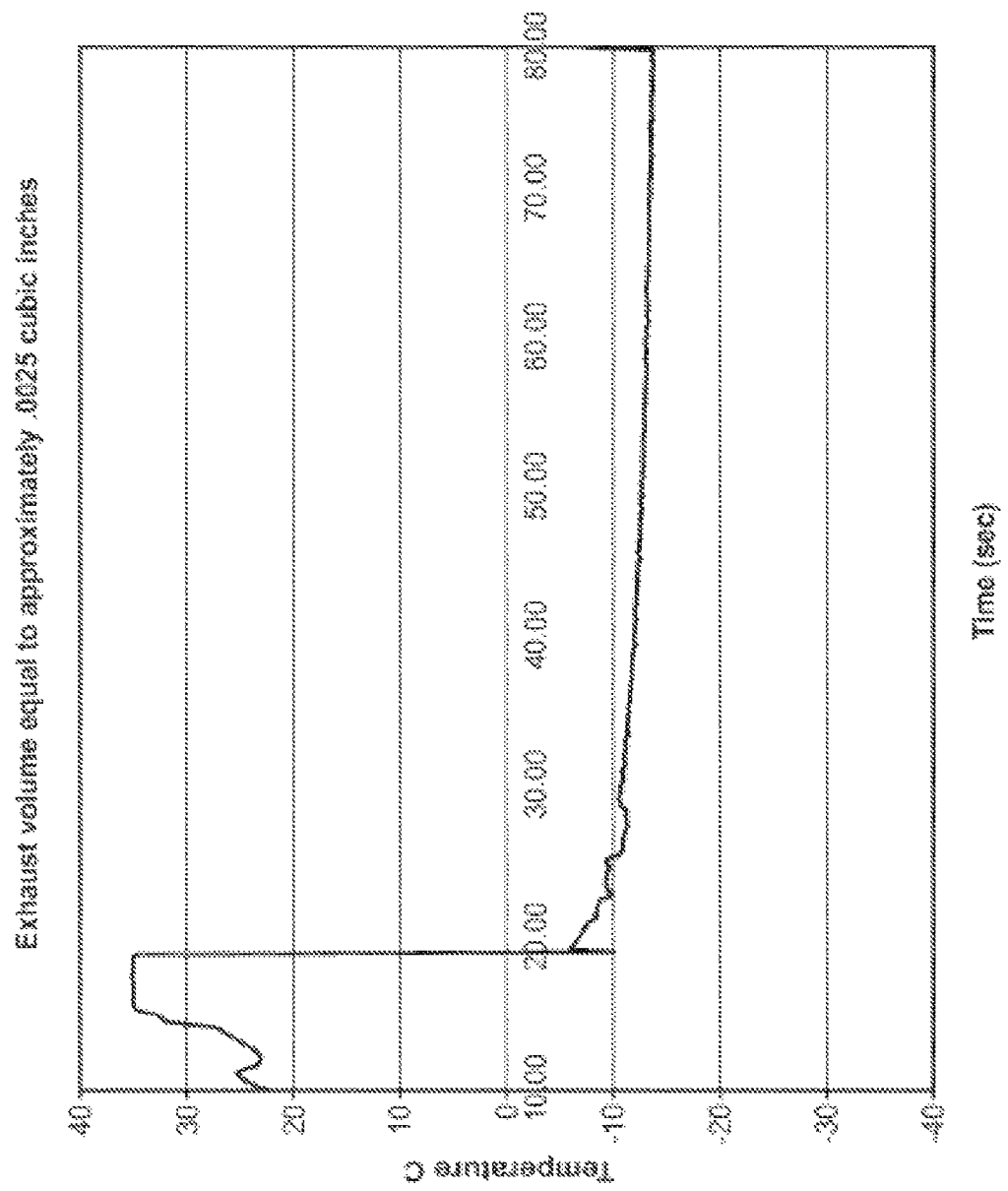
Figure 13D:
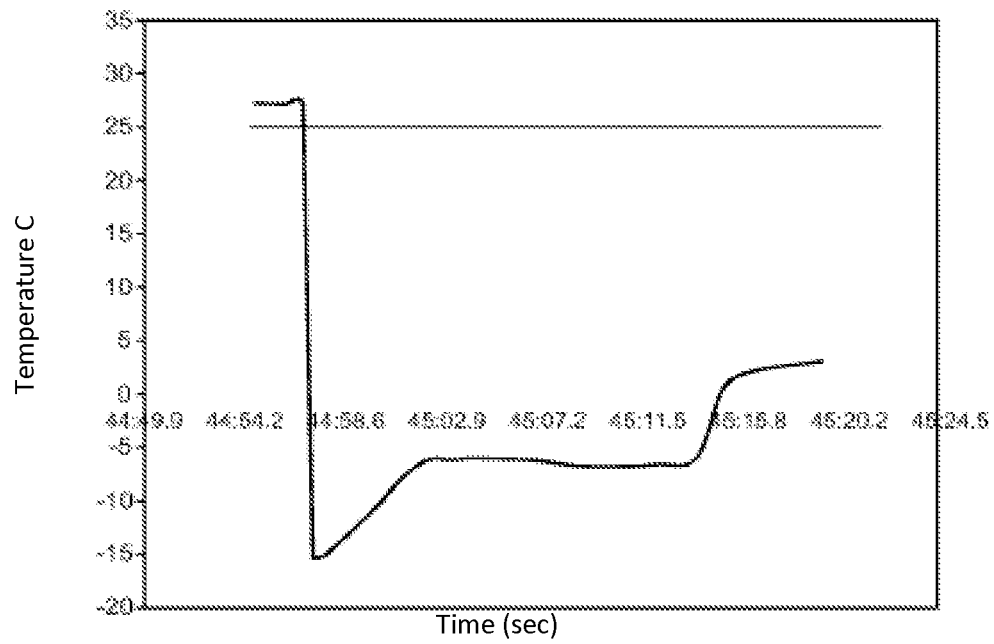

FIGS. 13A-13C present additional details on the effects of exhaust volume on cooling transients. In each case, a graph of temperature over time is shown for the outside temperature of an in vivo 30 g cooling needle with a target temperature of about −12° C. The devices were constructed with different exhaust volumes, with the volume being greater than about 0.009 in$^3$ in the embodiment of FIG. 13A. The embodiment of FIGS. 13B and 13C had exhaust volumes of about 0.009 in$^3$ and about 0.0025 in$^3$, respectively. The data collection rate was about 0.7 sec for the embodiment of FIG. 13A, while the embodiments of FIGS. 13B and 13C both had data collection rates of about 0.1 sec, so that the actual nadir for the embodiment of FIG. 13A may have actually been significantly lower than that shown. Regardless, the exhaust volume is preferably less than about 0.05 in$^3$, typically being less than 0.01 in$^3$ and/or 0.009 in$^3$, and ideally being less than 0.005 in$^3$.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow.

Figure 5A:
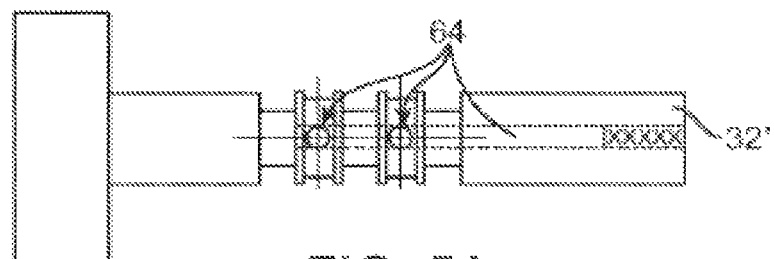
FIGS. 5A-5C illustrate an exemplary supply valve for use in the probe and system of FIGS. 1A and 1B.
Figure 5B:
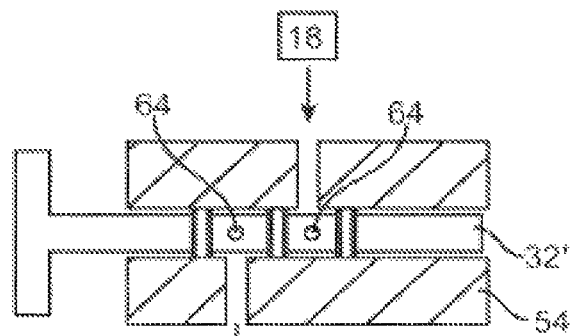
Figure 5C:
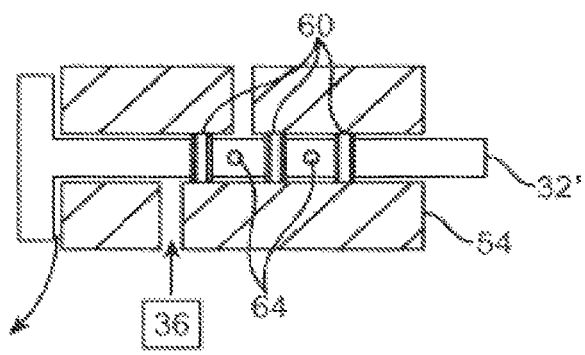

Additional aspects of the exemplary supply valves 32 can be understood with reference to FIGS. 2, 3, and 5A-5C. In FIG. 3, the valve is shown in the "on" configuration, with O-rings 60 sealing either side of the cooling fluid flow path and the cooling fluid flowing around the movable valve member. In FIGS. 5A-5C, the cooling fluid flows through a passage 64 that extends axially along an alternative valve body of valve body 32' when the valve is in the on configuration (seen in FIG. 5B), with the O-rings being disposed between recesses in the movable valve body so as to allow the valve to operate when the valve body is in any rotational orientation about its axis. In both embodiments, the cooling fluid flow path downstream of the valve is vented when the valve is in the "off" configuration (in the embodiment of FIG. 3, by channel 66, and in the embodiment of FIGS. 5A-5C by the vaporizing cooling fluid flowing through the annular space between the valve body and the adjacent housing 54 so as to preserve the cooling fluid within the movable valve body).

Venting of the cooling fluid from the cooling fluid supply tube 36 when the cooling fluid flow is halted by supply valve 32, 32' is advantageous to provide a rapid halt to the cooling of needle 26. For example, a 2.5 cm long 30 g needle cooled to an outside temperature of −15° C. might use only about 0.003 g/sec of nitrous oxide after the system approaches or reaches steady state (for example, 10 seconds after initiation of cooling). If the total volume along the cooling fluid path from supply valve to the distal end or release port of supply tube 36 is about 0.1 cc, the minim time to flow all the vaporizing liquid through the supply tube might be calculated as follows:

$$0.1 \text{ cc} * (0.7 \text{ g/cc}) = 0.07 \text{ g of liquid nitrous oxide,}$$

$$0.07 \text{ g}/(0.003 \text{ g/sec}) = 23 \text{ sec.}$$

Figure 10:
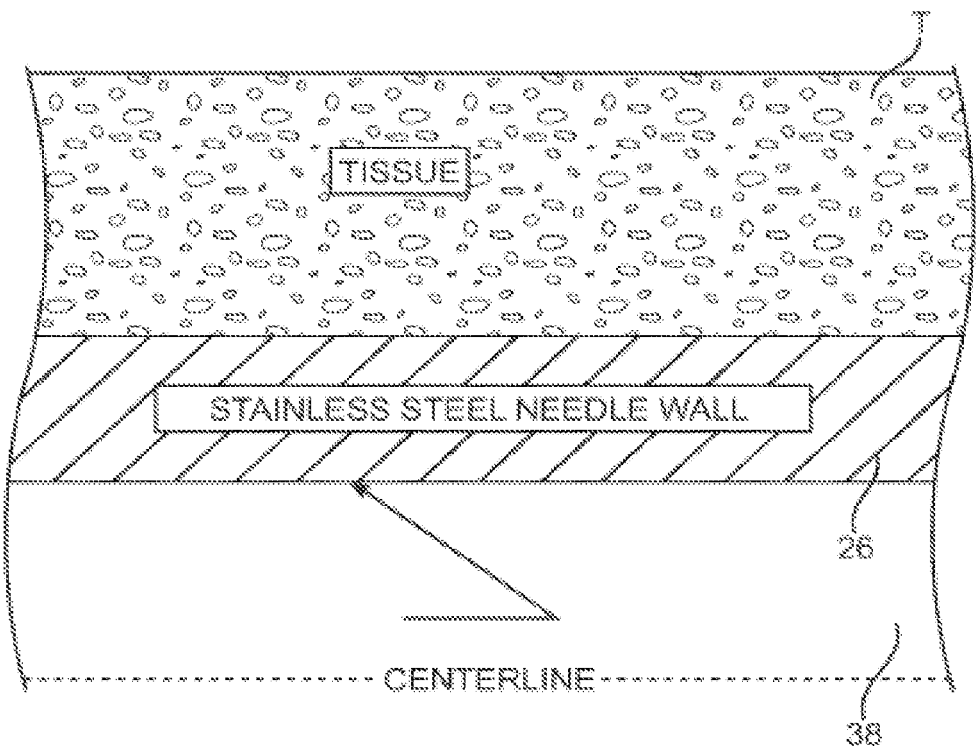
FIG. 10 schematically illustrates a thermal model of a cryogenic microprobe needle.
Figure 10A:
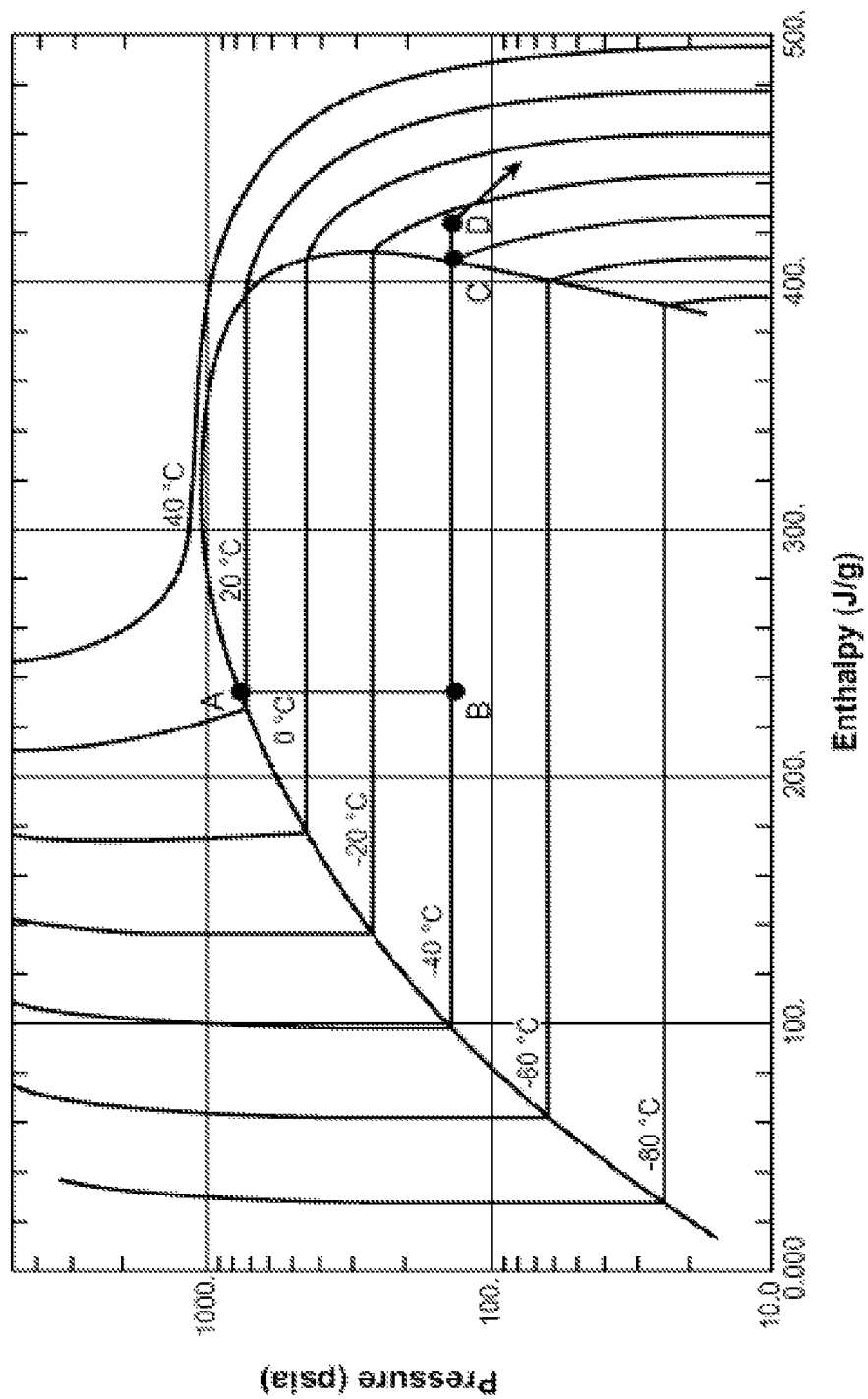
FIGS. 10A-10C graphically illustrate aspects of cryogenic cooling using nitrous oxide in the microprobe needles described herein.
Figure 10B:
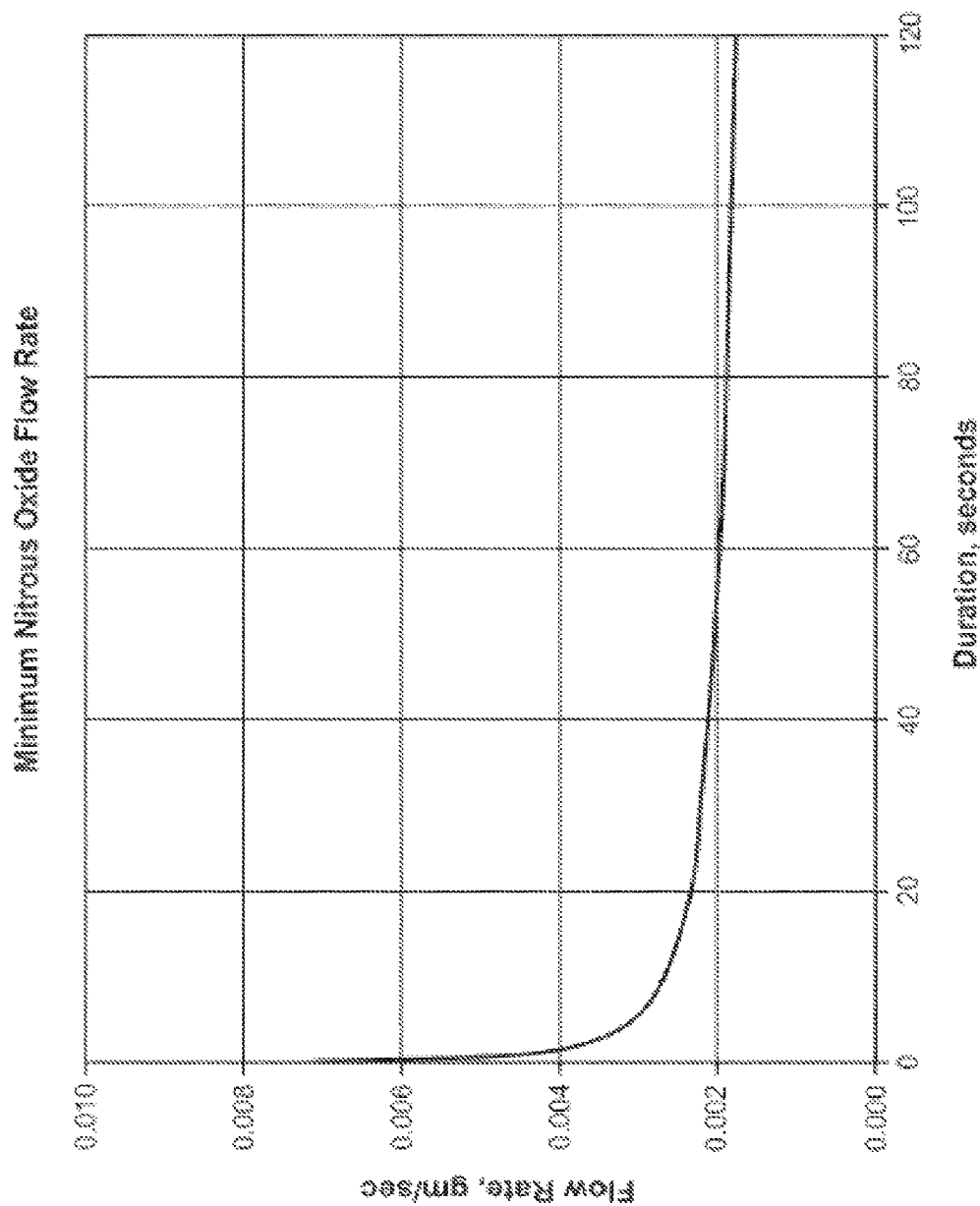
Figure 10C:
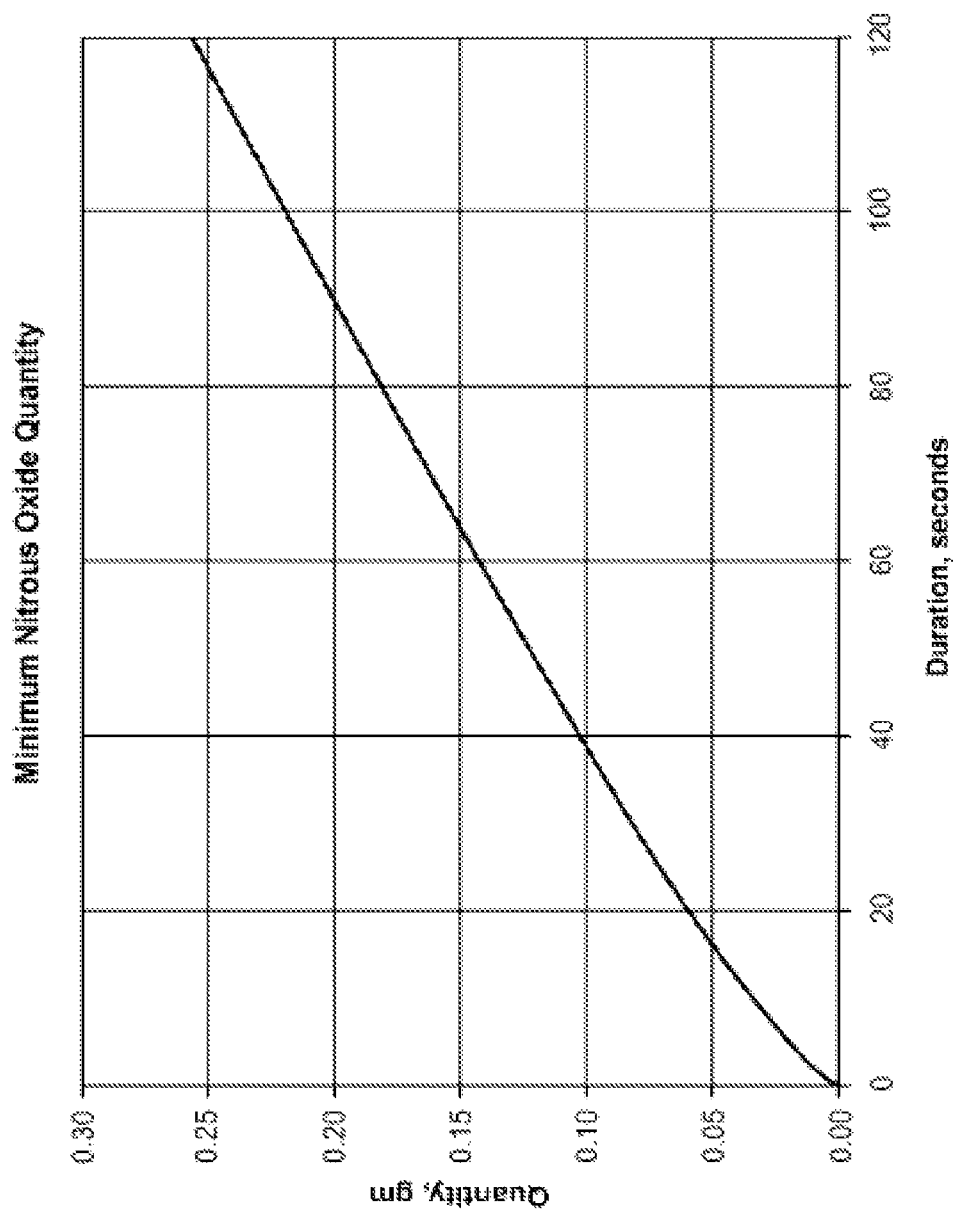

These calculation assume a fused silica supply tube sized to allow the minimum flow of nitrous oxide when fluid supply has a pressure of about 900 psi. When the supply valve is shut off, the pressure on the needle side of the supply valve would decay, causing the actual residual run time to be longer, with only a partial cooling near the distal tip of needle 16. Regardless, it is desirable to limit the flow of cooling fluid into the needle to or near that which will vaporize in the needle so as to facilitate use of a simple disposable cooling fluid supply cartridge 18. Analytical models that may be used to derive these cooling flows include that illustrated in FIG. 10, which may be combined with the properties of the cooling fluid (such as the pressure/enthalpy diagram of nitrous oxide seen in FIG. 10A) and the thermal properties of tissue shown in Table I to determine theoretical minimum cooling fluid flow rates (see FIG. 10B), theoretical minimum cooling fluid quantities (see FIG. 10C), and the like.

TABLE I

| Property | Units | Value |
|---|---|---|
| Upper temperature bond of freezing ($T_2$) | ° C. | −1 |
| Peak of phase transition temperature ($T_3$) | ° C. | −3 |
| Lower Temperature bond of freezing ($T_1$) | ° C. | −8 |
| Thermal conductivity in unfrozen region ($k_u$) | W/(mm-° C.) | 0.00063 |
| Thermal conductivity in frozen region ($k_f$) | W/(mm-° C.) | 0.00151 |
| Volumetric specific heat in unfrozen region ($\{\rho_t c_{t,f}\}$) | J/(mm$^3$-° C.) | 0.00316 |
| Volumetric specific heat in frozen region ($\{\rho_t c_{t,f}\}$) | J/mm$^3$-° C. | 0.00193 |
| Latent heat of solidification (HF) | J/mm$^3$ | 0.300 |

Referring now to FIGS. 3 and 4, a wide variety of alternative embodiments and refinements may be provided. Fluid supply 18 may be initially opened for use by penetrating a frangible seal of the cartridge with a pierce point 70 (such as by tightening a threaded cartridge support coupled to housing 54), with the nitrous being filtered by a filter 72 before being transmitted further along the cooling fluid path. Suitable filters may have pore sizes of from about 6 to about 25 μm, and may be available commercially from Porex of Georgia (or a variety of alternative suppliers), or may comprise a fine stainless steel screen (such as those having a mesh size of 635 with 0.0009" wire and spacing between the wire edges of approximately 0.0006"), or the like. A wide variety of epoxy or other adhesives 74 may be used, and the replaceable needle housing 24A and other structural components may comprise a wide variety of metals or polymers, including brass or the like. Fins 76 may be included to help vaporize excess cooling liquid traveling proximally of the insertable length of needle 26.

Very fine needles will typically be used to deliver to cooling at and/or below the surface of the skin. These needles can be damaged relatively easily if they strike a bone, or may otherwise be damaged or deformed before or during use. Fine needles well help inhibit damage to the skin during insertion, but may not be suitable for repeated insertion for treatment of numerous treatment sites or lesions of a particular patient, or for sequential treatment of a large area of the patient. Hence, the structures shown in FIGS. 1B, 3, and 4 allow the use probe bodies 16, 54 with a plurality of sequentially replaceable needles. O-rings 60 help to isolate the cooling fluid supply flow (which may be at pressures of up to about 900 psi) from the exhaust gas (which may be at a controlled pressure in a range between about 50 and 400 psi, depending on the desired temperature). Exemplary O-rings may comprise hydrogenated Buna-N O-rings, or the like.

Figures 11A, 11B:
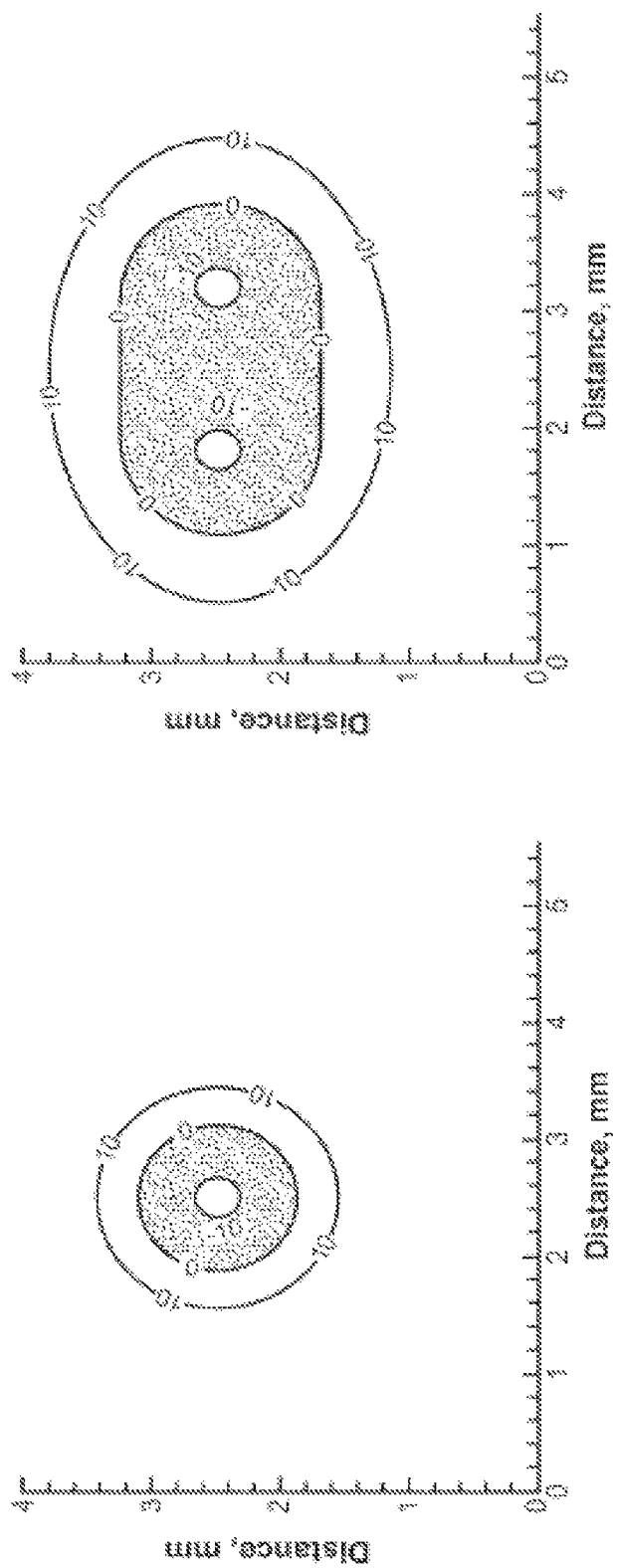
FIGS. 11A and 11B schematically illustrate cross-sectional views cooling with a one needle system and a multiple needle system.

It may be advantageous to increase the volume of tissue treated by a single treatment cycle. As it is often desirable to avoid increasing the needle size excessively, along with selecting needles of different lengths, needle assemblies having differing numbers of needles in a needle array may also be selected and mounted on the probe body. Other embodiments may employ a single needle array fixedly mounted to the probe body, or a plurality of replaceable needle assemblies which all include the same number of needles. Regardless, cooling fluid flow to a plurality of needles may be provided, for example, by inserting and bonding a plurality of fused silica supply tubes into a 0.010 polyimide tubing 58 or header within the needle assembly, and by advancing the distal end of each supply tube into a lumen of an associated needle 26. The needles might vent into a common exhaust space coaxially around polyimide tubing 58 in a manner similar to the single needle design shown. This can increase the quantity of tissue treated adjacent and/or between needles, as can be seen by comparing the theoretical 15 second exposures to one and two needles having a −15° C. probe surface, as shown in FIGS. 11A and 11B, respectively.

Figure 6A:
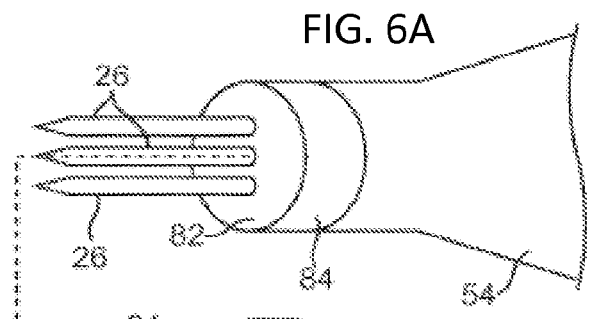
FIGS. 6-8 illustrate skin-engaging surfaces that selectably limit an effective insertable length of the needle, that apply pain-dulling pressure, and that apply inflammation-inhibiting cooling to the skin before and/or during treatment of the target tissue, respectively.
Figure 6B:
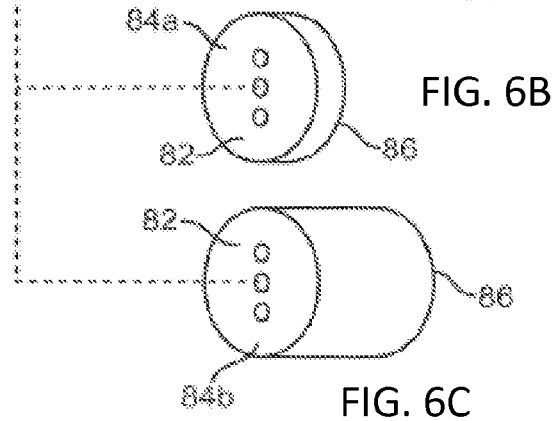
Figure 6C:
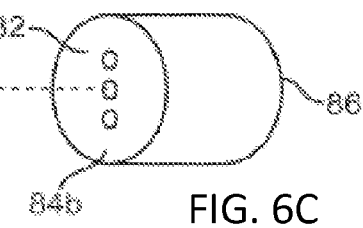

Referring now to FIGS. 6A-6C, it may be desirable to allow a system user to select a treatment depth, and/or to treat the skin surface to a temperature similar to that of the underlying target tissue along needle 26. A distally oriented surface 82 supported by probe body 54 adjacent and/or around the proximal end of the needles may be configured to limit heat transfer to or from the skin when the needle 26 is inserted so that surface 82 engages the skin and cooling fluid flows into the needle. Exemplary heat transfer limiting surfaces may be formed, for example, from a small rigid foam pad or body 84. Closed cell polyethylene foam or Styrofoam™ foam bodies may be used. As seen in FIGS. 6B-6C, an alternatively selectable set of bodies may also have differing thicknesses between the skin engaging-surface 82 and a surface 86 that engages the distal portion of the probe body. A user can then select an insertable length of the needle by selecting an appropriate probe body 84, 84a, 84b and mounting the selected probe body onto the needles. Skin engaging surface 82 of bodies 84, 84a, and 84b (or some other skin engaging surface adjacent the distal end of the needle) may be used to apply pressure to the skin, lesion, and/or target tissue during treatment. Alternative intertable length varying arrangements may also be provided, including those having threaded or other articulatable structures supporting the skin engaging surface 82 relative to the adjacent probe body 54 and the like.

Figure 7:
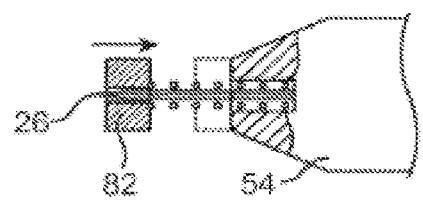

Referring now to FIG. 7, the application of pressure before, during, and/or after cooling may help dull or otherwise inhibit sharp pain. Such pain may otherwise result from the skin penetration, cooling, or thawing of the target and/or collateral tissues. It may also be beneficial to obscure the patient's view of the cooling needles, and/or to cover the needles when not in use so as to inhibit needle-stick injuries and potential disease transmission. Toward that end, skin-engaging surface 82 may be supported by an articulatable support structure having a first configuration (shown in solid in FIG. 7) and a second configuration (shown dashed in FIG. 7). A simple spring mechanism may be used to apply a desired contact force between the skin-engaging surface 82 and the patient before insertion and during cooling. More sophisticated arrangements can also be employed in which the needle is driven distally and then proximally relative to the skin engaging surface appropriate times after sufficient pressure is applied to the patient, and the like.

Figure 8:
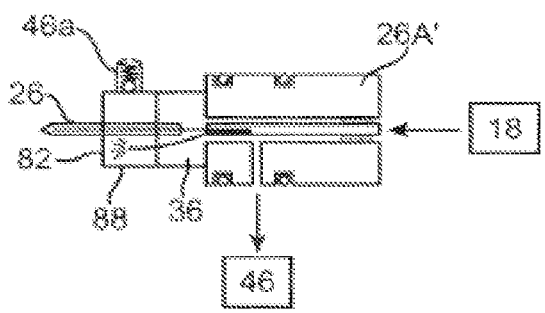
Figure 14:
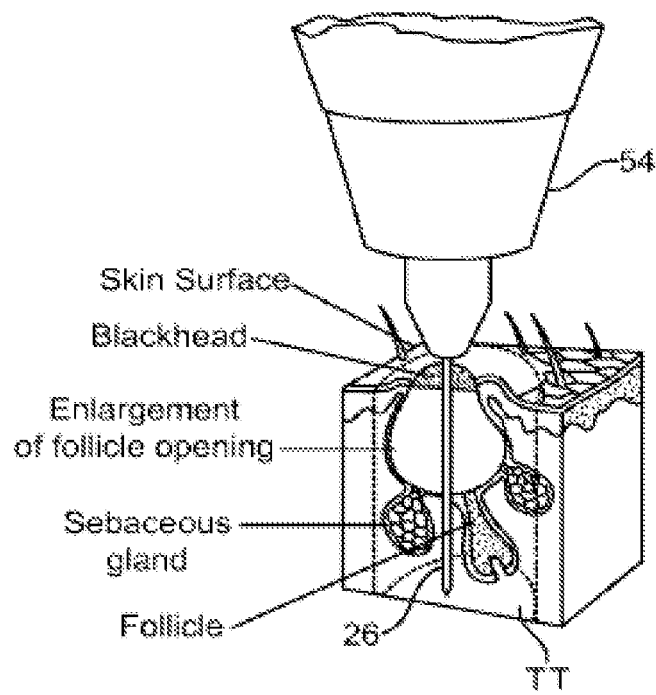
FIG. 14 schematically illustrates a cryogenic microprobe needle system being used for a dermatological treatment.

Referring now to FIG. 8, still further alternative embodiments may be provided, in this case to apply different cooling temperatures to the patient, and/or to apply cooling to the skin surface and to a target tissue adjacent needle 26. For example, in the case of acne it may be desirable to have two different cooling target temperatures, with cooling on the skin surface to inhibit inflammation (such as to about −10° C.), and (see FIG. 14) cooling of a target tissue TT cylinder around needle 26 sufficient to kill bacteria in the sebaceous gland and enlarged follicle opening (such as to about −20° C.). This dual temperature treatment may be particularly beneficial for severe forms of acne involving cysts or nodules. To provide cooling of tissue engaging surface 82, that surface may be thermally coupled to a chamber 88. Cooling fluid may be transmitted into chamber 88 by a port of a cooling fluid supply tube 36, and the pressure of chamber 88 (and hence the temperature within the chamber) can optionally be controlled by a dedicated additional pressure relief valve 46a. As the pressure within chamber 88 may differ from that within the needle, different treatment temperatures may be provided. The structures described herein can also be combined, for example, with the dual skin surface/needle temperature treatment structure of FIG. 8 being compatible with the replaceable needle systems of FIGS. 1B, 3, and/or 4. The dual skin surface/needle treatment systems and methods may also be compatible, for example, with the articulatable skin surface supports of FIG. 7 so as to apply cooled pressure to the skin prior to and/or during needle insertion using a flexible fluid supply tube or the like.

Still further alternatives may also be provided, including systems that generate a high rate of cooling to promote necrosis of malignant lesions or the like. High cooling rates limit osmotic effects in the target tissue. Slow cooling may tend to promote ice formation between cells rather than within cells due to the osmotic effect. While such slow cooling can be provided where necrosis is not desired (such as through the use of a proportion supply valve to modulate flow, a processor generated on/off cycle during initial cooling, or the like), the needle probes described herein will often be well suited to induce rapid cooling rates of the target tissue by vaporizing the cooling fluid in close thermal and spatial proximity to that target tissue. Hence, where necrosis of cells by intracellular ice formation is desired, cooling rates of about 25° C./sec or more, or even about 50° C./sec or more can be provided.

Figure 9:
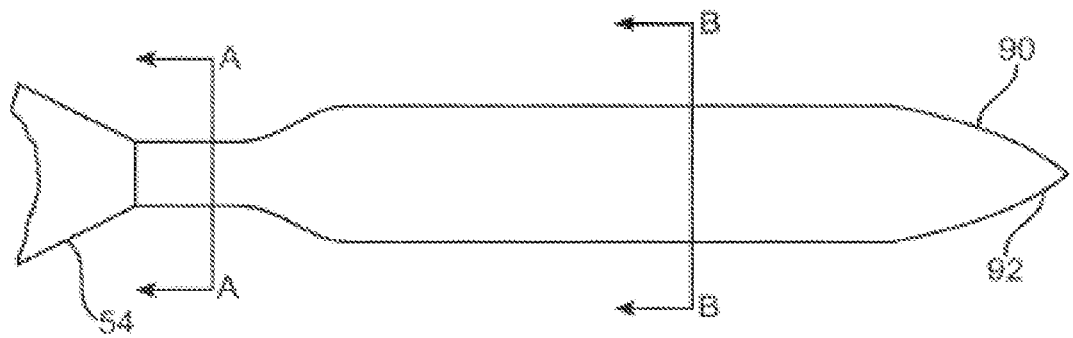
FIGS. 9, 9A, and 9B schematically illustrate a needle having an elongate cross-section to enhance the volume of treated tissue.
Figure 9A:
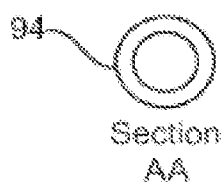
Figure 9B:
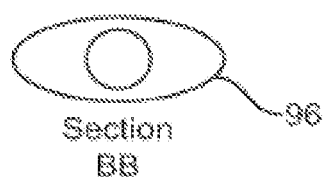

Referring now to FIGS. 9, 9A, and 9B, needles having circular cross-sectional shapes can often be used, but may not always provide the desired surface area for the cross-sectional area of the needle. Increased surface area may decrease the amount of time the needle is inserted to cool a volume of tissue to a temperature in a target range. Hence, a needle with an elongate outer cross-section such as elliptical needle 90 may be desirable. A distal cutting edge 92 at the distal tip may facilitate insertion and a circular cross-section 94 near the proximal end may limit cooling adjacent the skin, while cooling of the target tissue therebetween is enhanced by elliptical cross-section 96.

Referring now to FIG. 15, a method 100 facilitates treating a patient using a cryogenic cooling system having a self-contained disposable handpiece and replaceable needles such as those of FIG. 1B. Method 100 generally begins with a determination 110 of the desired tissue remodeling and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined 114. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

As described above, pressure, cooling, or both may be applied 118 to the skin surface adjacent the needle insertion site before, during, and/or after insertion 120 and cryogenic cooling 122 of the needle and associated target tissue. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply cartridge included in the self-contained handpiece is depleted, the used handpiece and needles can be disposed of 130.

A variety of target treatment temperatures, times, and cycles may be applied to differing target tissues to as to achieve the desired remodeling. For example, (as more fully described in patent application Ser. No. 11/295,204, previously incorporated herein by reference) desired temperature ranges to temporarily and/or permanently disable muscle, as well as protect the skin and surrounding tissues, may be indicated by Table III as follows:

TABLE II

| Temperature | Skin | Muscle/Fat |
|---|---|---|
| 37° C. | baseline | baseline |
| 25° C. | cold sensation | |
| 18° C. | reflex vasodilation of deep blood vessels | |
| 15° C. | cold pain sensation | |
| 12° C. | reduction of spasticity | |
| 10° C. | very cold sensation reduction of chronic oedema Hunting response | |
| 5° C. | pain sensation | |
| 0° C. | freezing point | |
| −1° C. | | Phase transition begins |
| −2° C. | | minimal apoptosis |
| −3° C. | | Peak phase transition |
| −5° C. | tissue damage | moderate apoptosis |
| −8° C. | | Completion of phase transition |
| −10° C. | | considerable apoptosis |
| −15° C. | | extensive apoptosis mild-moderate necrosis |
| −40° C. | | extensive necrosis |

To provide tissue remodeling with a desired or selected efficacy duration, tissue treatment temperatures may be employed per Table III as follows:

TABLE III

| Cooled Temperature Range | Time Effectiveness | Purpose |
|---|---|---|
| ≥0° C. | Treatment lasts only while the needle is inserted into the target tissue. | Can be used to identify target tissues. |
| From 0° C. to −5° C. | Often lasts days or weeks, and target tissue can repair itself. Embodiments may last hours or days. | Temporary treatment. Can be used to evaluate effectiveness of remodeling treatment on skin surface shape or the like. |
| From −5° C. to −15° C. | Often lasts months to years; and may be permanent. Limited muscle repair. Embodiments may last weeks to months. | Long term, potentially permanent cosmetic benefits. Can be deployed in limited doses over to time to achieve staged impact, controlling outcome and avoiding negative outcome. May be employed as the standard treatment. |
| From −15° C. to −25° C. | Often lasts weeks or months. Muscle may repair itself via satellite cell mobilization, Embodiments may last years. | May result in Mid-term cosmetic benefits, and can be used where permanent effects are not desired or to evaluate outcomes of potentially permanent dosing. Embodiments may provide permanent treatment. |

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of these apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

While the exemplary embodiments have been described in some detail for clarity of understanding and by way of example, a number of modifications, changes, and adaptations may be implemented and/or will be obvious to those as skilled in the art. For example, one or more temperature feedback loops may be used to control the treatments, with the tissue temperature optionally being taken using a temperature sensing needle having a temperature sensor disposed adjacent an outer cooled skin engaging surface of the needle. Hence, the scope of the present invention is limited solely by the independent claims.

What is claimed is:

1. A system for treating a target tissue of a patient, the system comprising:
   a first having a proximal end, an axially sealed distal tissue penetrating end, and a lumen therebetween, the first needle comprising a 16 gauge or smaller needle size;
   a first cooling fluid supply lumen extending distally within the first needle lumen to a distal portion of the first needle lumen, the first supply lumen defined by a first supply tube comprising fused silica and wherein the first supply tube within the needle further includes a polymer over the fused silica;
   a cooling fluid source coupleable to the first supply lumen to direct cooling fluid flow into the first needle lumen so that liquid from the cooling flow vaporizes within the target tissue when the first needle extends into the target tissue;
   a handpiece body supporting the needle;
   at least one distally oriented skin engaging surface supported by the handpiece body so as to engage the skin surface before, during and/or after cooling of the target tissue; and
   wherein the skin-engaging surface comprises a cooled tissue engaging surface.

2. The system of claim 1, wherein an outer diameter of the polymer is less than 800 μm.

3. The system of claim 1, wherein the supply tube extends in cantilever distally into the needle lumen, and wherein the supply tube has sufficient stiffness to inhibit flow induced buckling of the supply tube within the needle lumen.

4. The system of claim 1, wherein the skin engaging surface inhibits heat transfer to or from the skin surface engaged thereby.

5. The system of claim 1, wherein an insertable length of the needle between the distal end of the needle and the at least one skin engaging surface is selectably alterable, the at least one skin engaging surface comprising a plurality of alternative skin engaging surfaces disposed on associated alternative spacer bodies, the spacer bodies having differing thicknesses between their skin engaging surfaces and an opposed handpiece engaging surface so that a user can alter the insertable length of the needle by selection from among the spacer bodies.

6. The system of claim 1, wherein the skin-engaging surface is thermally coupled to a skin cooling chamber, and wherein a skin cooling port directs cooling fluid from the fluid source into the skin cooling chamber, the skin cooling chamber having a higher operating pressure than the needle lumen.

7. The system of claim 1, wherein the skin engaging surface is configured to cool the skin to inhibit inflammation, and wherein the needle is configured to cool the target tissue to below 0° C. to induce necrosis.

8. The system of 1, wherein a controller is coupled with the needle lumen by a valve, the controller having a first configuration for providing an initial cooling state and a second configuration for providing a treatment temperature in a target range by establishing a target treatment pressure in the lumen, the initial cooling state configured to induce gradual cooling of the needle using an intermediate treatment pressure in the needle lumen that is higher than the target treatment pressure so as to allow osmotic effects to inhibit intracellular ice formation and necrosis of the tissue.

9. The system of claim 1, wherein the cooling fluid, when vaporizing within the needle lumen cools an outer surface of the needle to a temperature in a treatment temperature range throughout an insertable length of the needle between the distal end and the proximal end such that a target tissue extending to the skin surfaces can be treated.

10. The system of claim 1, wherein the supply lumen is defined by a non-metallic tubular supply tube.

11. The system of claim 1, wherein the system has a first configuration and a second configuration, the skin engaging surface in the first configuration disposed distally of the needle so as to engage the skin before penetrating the target tissue, the needle in the second configuration extending distally of the skin engaging surface.

12. The system of claim 11, further comprising an articulatable support coupling the skin engaging surface to the needle so the skin engaging surface applies a pain inhibiting pressure to the skin before, during, and/or after skin penetration by the needle.

13. The system of claim 1, wherein, when the flow is initiated and when an outer surface of the needle engages the target tissue, the outer surface of the needle engaging the target tissue cools at a rate of more than about 25° C./sec so as to promote intracellular ice formation and necrosis of the target tissue.

14. The system of claim 13, further comprising an array of needles coupled to the fluid source, each needle, when the flow is initiated, having an outer surface that cools at a rate of more than about 25° C./sec so as to promote intracellular ice formation and necrosis of the target tissue between the needles when the flow is initiated and when an outer surface of the needle engages the target tissue.

15. The system of claim 1, wherein an outer surface of the needle has an elongate cross-section.

16. The system of claim 15, wherein a proximal cross-section of the needle is circular to limit cooling adjacent the skin, the elongate cross-section comprising an elliptical cross-section to enhance heating along the target tissue, and wherein the distal end of the needle has a sharpened cutting edge.

17. The system of claim 1, wherein the needle is metallic.

18. The system of claim 17, further comprising:
a second needle having a proximal end, an axially sealed distal tissue penetrating end, and a lumen therebetween, the second needle comprising a 16 gauge or smaller needle size;
a second cooling fluid supply lumen extending distally within the second needle lumen to a distal portion of the second needle lumen, the second supply lumen defined by a second supply tube comprising fused silica and wherein the second supply tube further has a polymer over the fused silica; and
wherein the cooling fluid source is coupleable to the second supply lumen simultaneously with the first supply lumen.

19. The system of claim 18, further comprising a handpiece body for housing the cooling fluid source and for supporting the first needle and second needle, the first needle spaced apart from the second needle, and wherein the first and second needle are removably supported by the handpiece body.

20. The system of claim 19, wherein the first and second cooling fluid supply lumens have an inner diameter of less than 50 µm.

21. The system of claim 1, wherein the needle comprises a 25 gauge or smaller needle size.

22. The system of claim 21, wherein the supply lumen has an inner diameter of less than 100 µm.

23. The system of claim 21, wherein an aspect ratio defined by an insertable length of the needle to an outer size of the needle is more than 20.

24. The system of claim 21, further comprising a handle supporting the needle, the supply lumen, and the fluid source for manual manipulation during treatment.

25. The system of claim 21, further comprising a supply valve disposed between the supply lumen and the fluid source, the system having a cooling fluid supply volume between the needle lumen and the supply valve, the valve having a first configuration and a second configuration, the valve in the first configuration providing fluid communication between the fluid source and the supply volume, the valve in the second configuration inhibiting the cooling flow and venting the supply volume so as to limit cooling fluid vaporization within the needle lumen after the valve moves from the first configuration to the second configuration.

26. The system of claim 21, further comprising a pressure relief valve in fluid communication with the needle lumen so as to control a pressure of the vaporizing cooling flow within the needle such that a temperature of the target tissue is within a desired treatment temperature range.

27. The system of claim 26, wherein an exhaust volume of the device between the supply lumen and the pressure relief valve is less than about 0.05 in$^3$.

28. The system of claim 26, wherein the flow is metered primarily by a flow resistance of the supply lumen, and the metered flow inhibits temperature fluctuation by maintaining a liquid/gas mixture within the needle lumen.

29. The system of claim 28, wherein the flow is not actively modulated between the fluid source and the needle lumen during cooling, wherein the pressure relief valve comprises a biasing spring mechanically urging a valve member against a valve seat so as to maintain pressure within the needle lumen within a desired pressure range, and wherein the biasing spring is disposed outside an exhaust volume extending from the supply lumen to the valve seat.

* * * * *